United States Patent [19]

Yagawara et al.

[11] Patent Number: 5,003,812

[45] Date of Patent: Apr. 2, 1991

[54] GAS DETECTING DEVICE

[75] Inventors: Shinji Yagawara, Yokohama; Junji Manaka, Kawasaki; Wasaburo Ohta, Yokohama, all of Japan

[73] Assignee: Ricoh Company, Ltd., Tokyo, Japan

[21] Appl. No.: 559,148

[22] Filed: Jul. 30, 1990

Related U.S. Application Data

[62] Division of Ser. No. 288,279, Dec. 22, 1988, Pat. No. 4,967,589.

[30] Foreign Application Priority Data

| Dec. 23, 1987 | [JP] | Japan | 62-325921 |
| Mar. 1, 1988 | [JP] | Japan | 63-48408 |
| Mar. 25, 1988 | [JP] | Japan | 63-71061 |
| May 10, 1988 | [JP] | Japan | 63-114372 |
| May 24, 1988 | [JP] | Japan | 63-126836 |
| May 24, 1988 | [JP] | Japan | 63-126837 |
| Jul. 6, 1988 | [JP] | Japan | 63-169534 |
| Dec. 6, 1988 | [JP] | Japan | 63-306850 |

[51] Int. Cl.$^5$ .......................... G01N 27/12
[52] U.S. Cl. .................... 73/31.06; 338/34; 422/98
[58] Field of Search ............... 73/31.06, 31.05, 25.05, 73/336.5; 338/34; 422/98

[56] References Cited

U.S. PATENT DOCUMENTS

| 4,224,280 | 9/1980 | Takahama et al. | 73/31.06 X |
| 4,358,950 | 11/1982 | Chang | 73/31.05 |
| 4,580,439 | 4/1986 | Manaka | 73/31.06 |
| 4,792,433 | 12/1988 | Katsura et al. | 73/31.06 X |

FOREIGN PATENT DOCUMENTS

61-191953 11/1986 Japan .

OTHER PUBLICATIONS

T. Oyabu, "Sensing Characteristics of SnO$_2$ Thin Film Gas Sensor", J. Appl. Phys., 53, 1982, pp. 2785–2787, (p. 65).

H. Ogawa et al., "Electrical Properties of Tin Oxide Ultrafine Particle Films", The Electrochemical Society, vol. 128, No. 9, pp. 2020–2025, 1981.

*Primary Examiner*—Hezron E. Williams
*Assistant Examiner*—Joseph W. Roskos
*Attorney, Agent, or Firm*—Oblon, Spivak, McClelland, Maier & Neustadt

[57] ABSTRACT

A gas detecting device includes a substrate, an insulator layer formed on the substrate, a gas sensitive layer formed the insulator layer, a pair of detection leads formed on the insulator layer, the gas sensitive layer partially overlying the pair of detection leads, a signal derived from the gas sensitive layer being sent to an external circuit through the pair of detection leads, a heater member arranged on the insulator layer in the vicinity of the gas sensitive layer, and an insulation coating layer formed on the pair of detection leads and the heater member, and partially overlying the gas sensitive layer so that the gas sensitive layer is put between the insulator layer and the insulation coating layer, and a portion of an upper surface of the gas sensitive layer is exposed to gas.

2 Claims, 45 Drawing Sheets

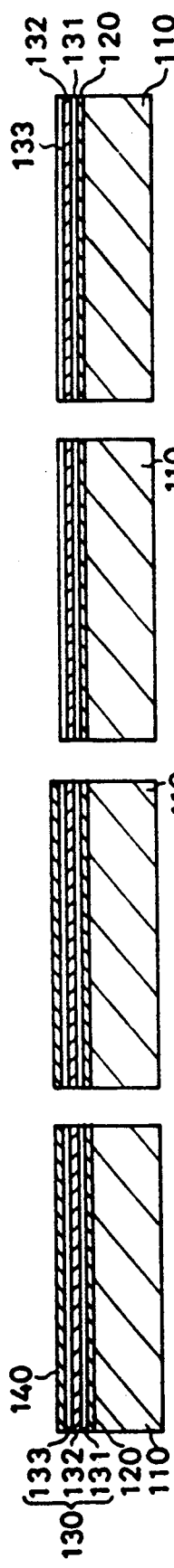
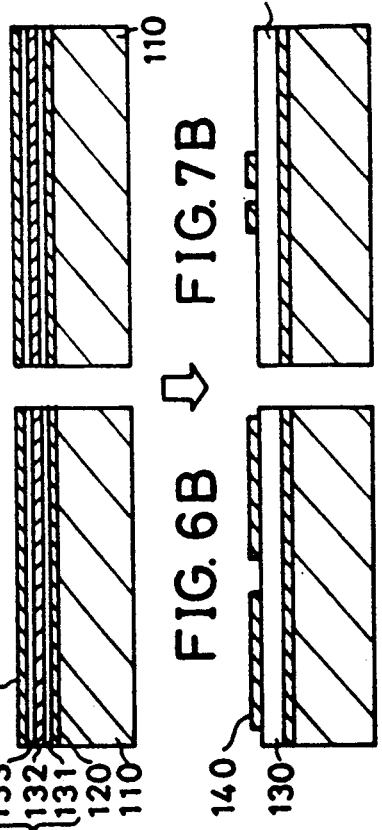
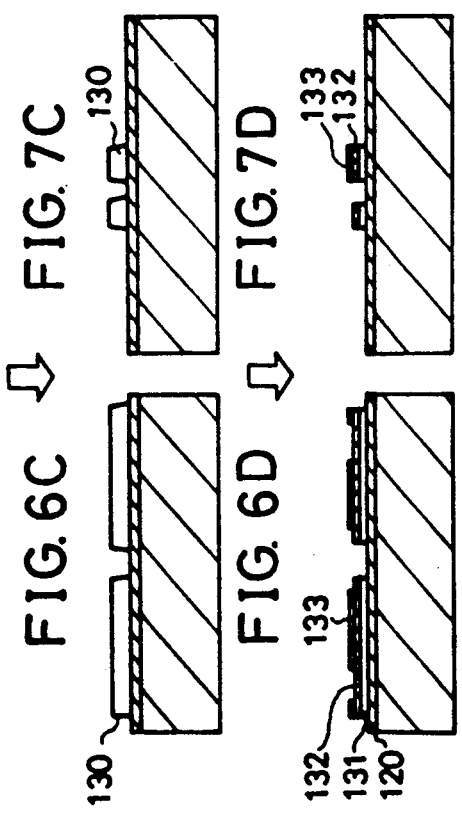
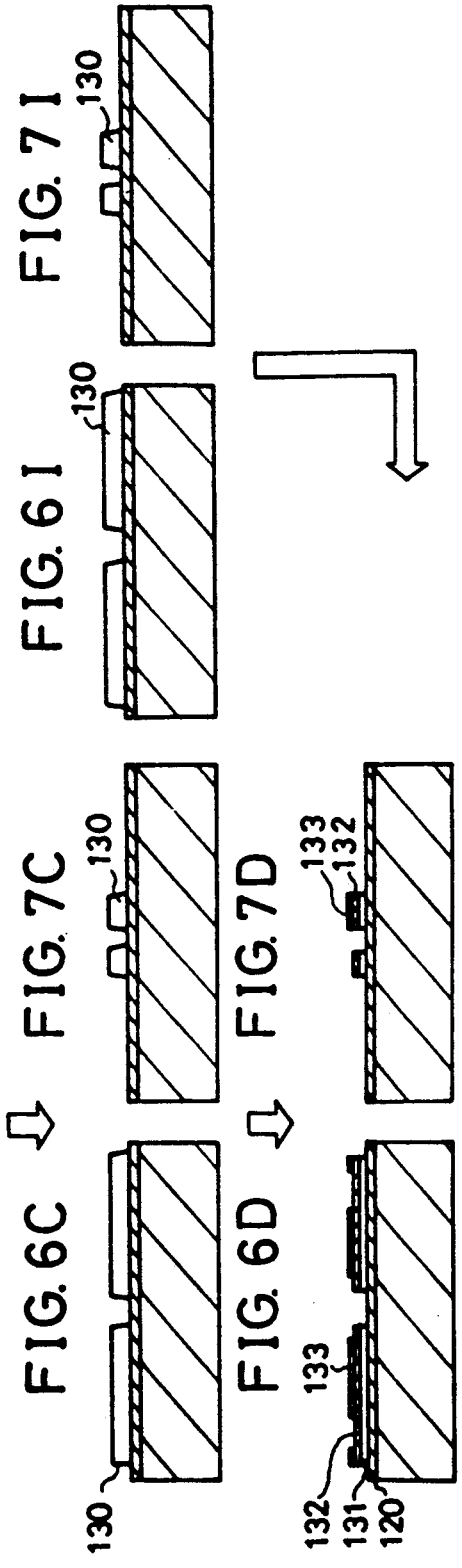

FIG. 6E  FIG. 7E
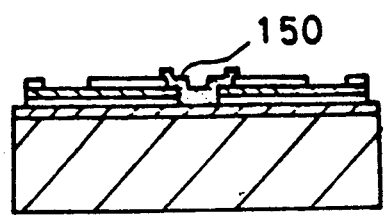 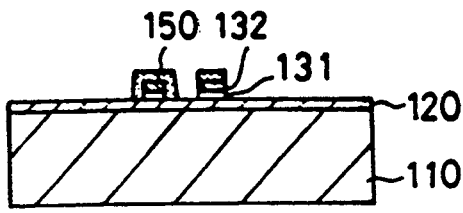
FIG. 6F  FIG. 7F
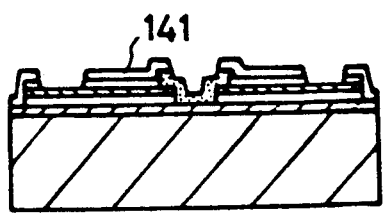 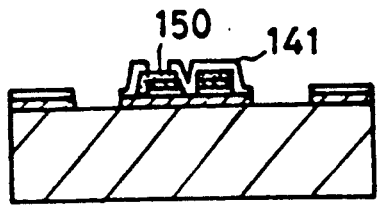
FIG. 6G  FIG. 7G
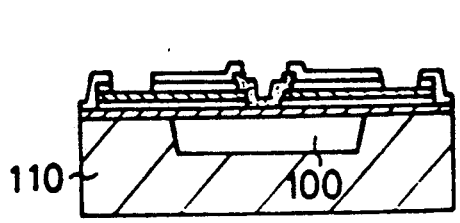 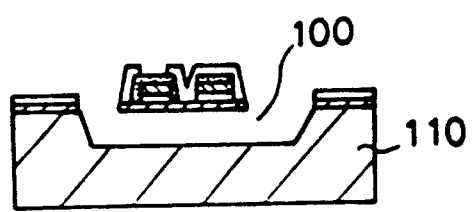

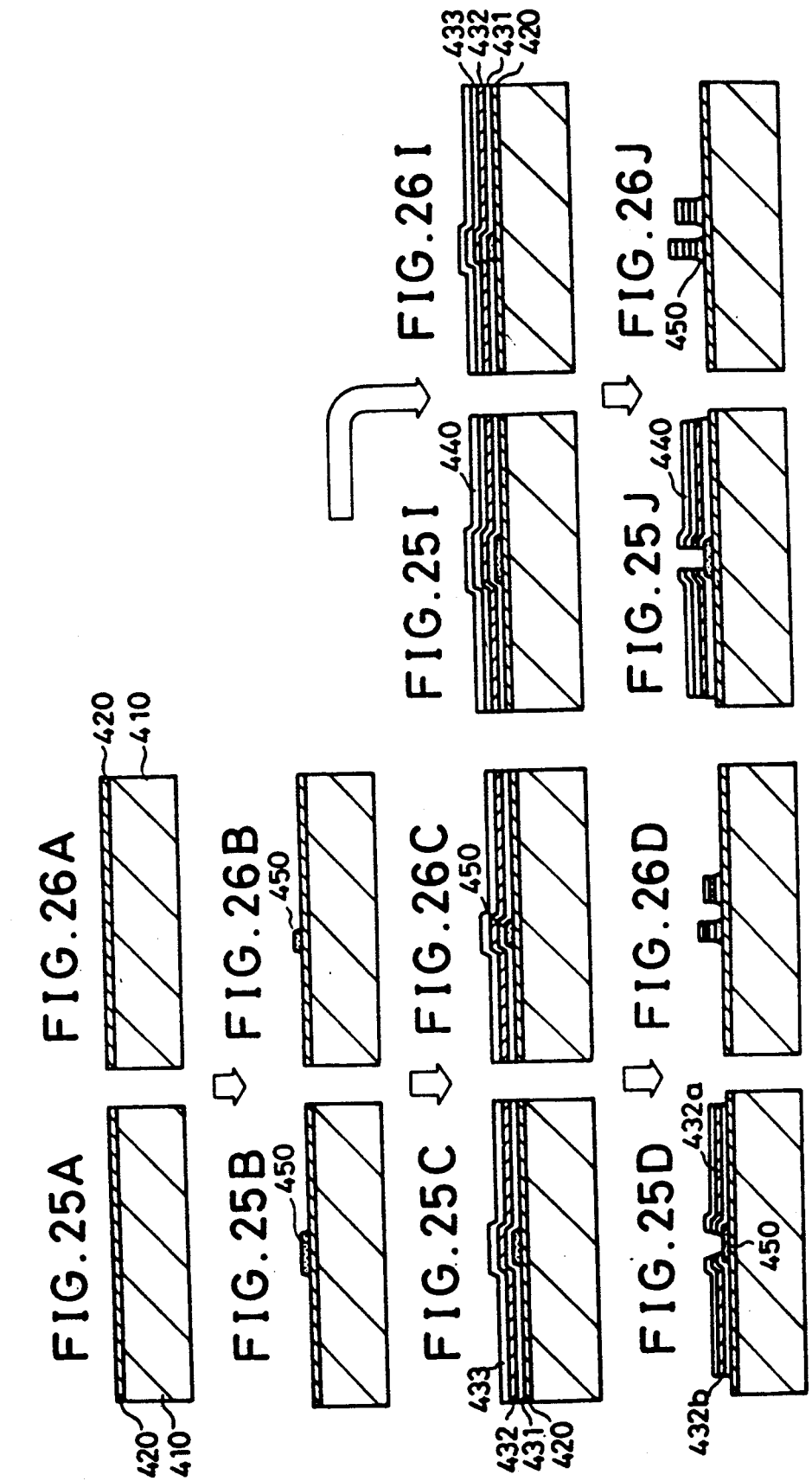

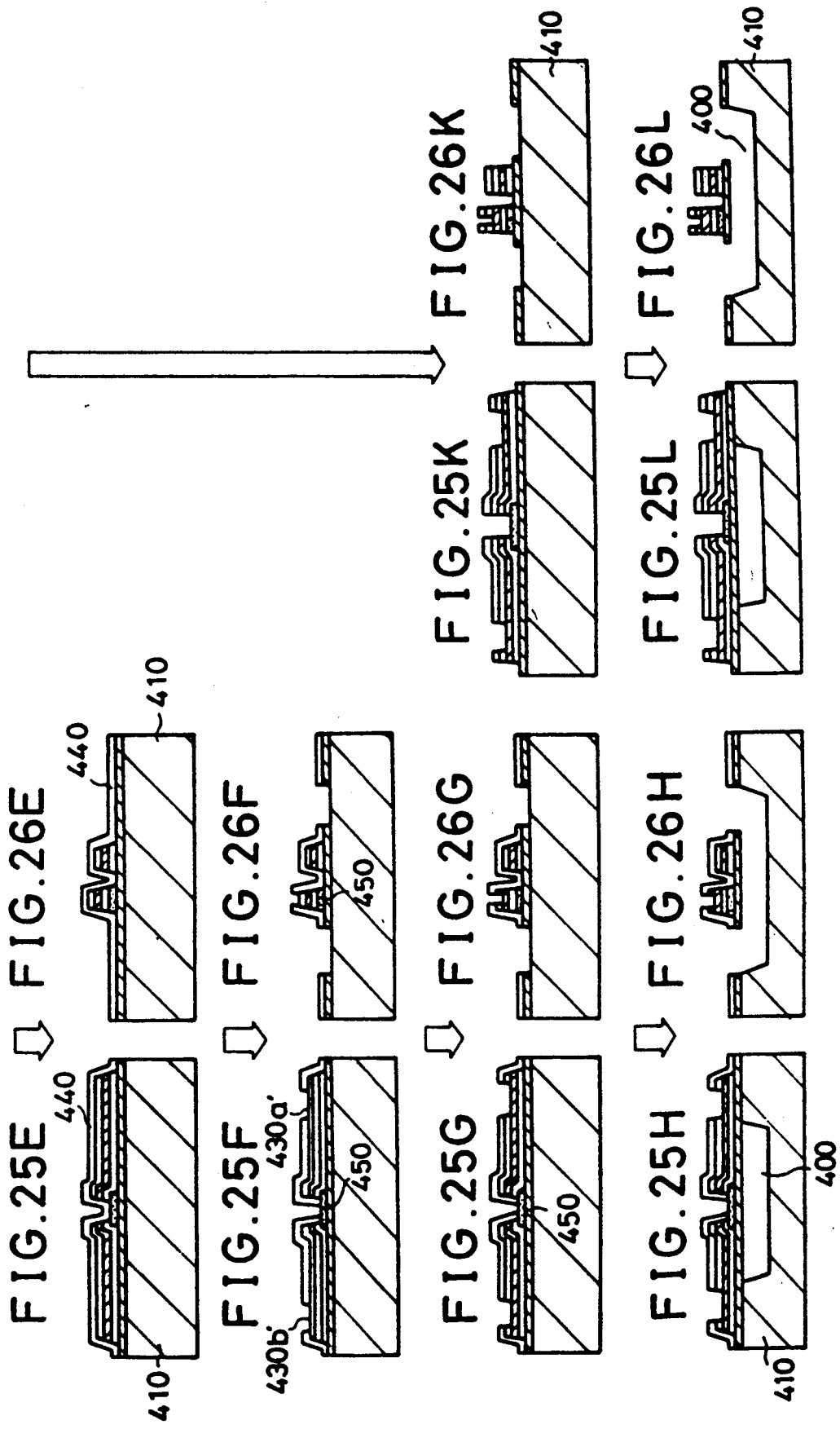

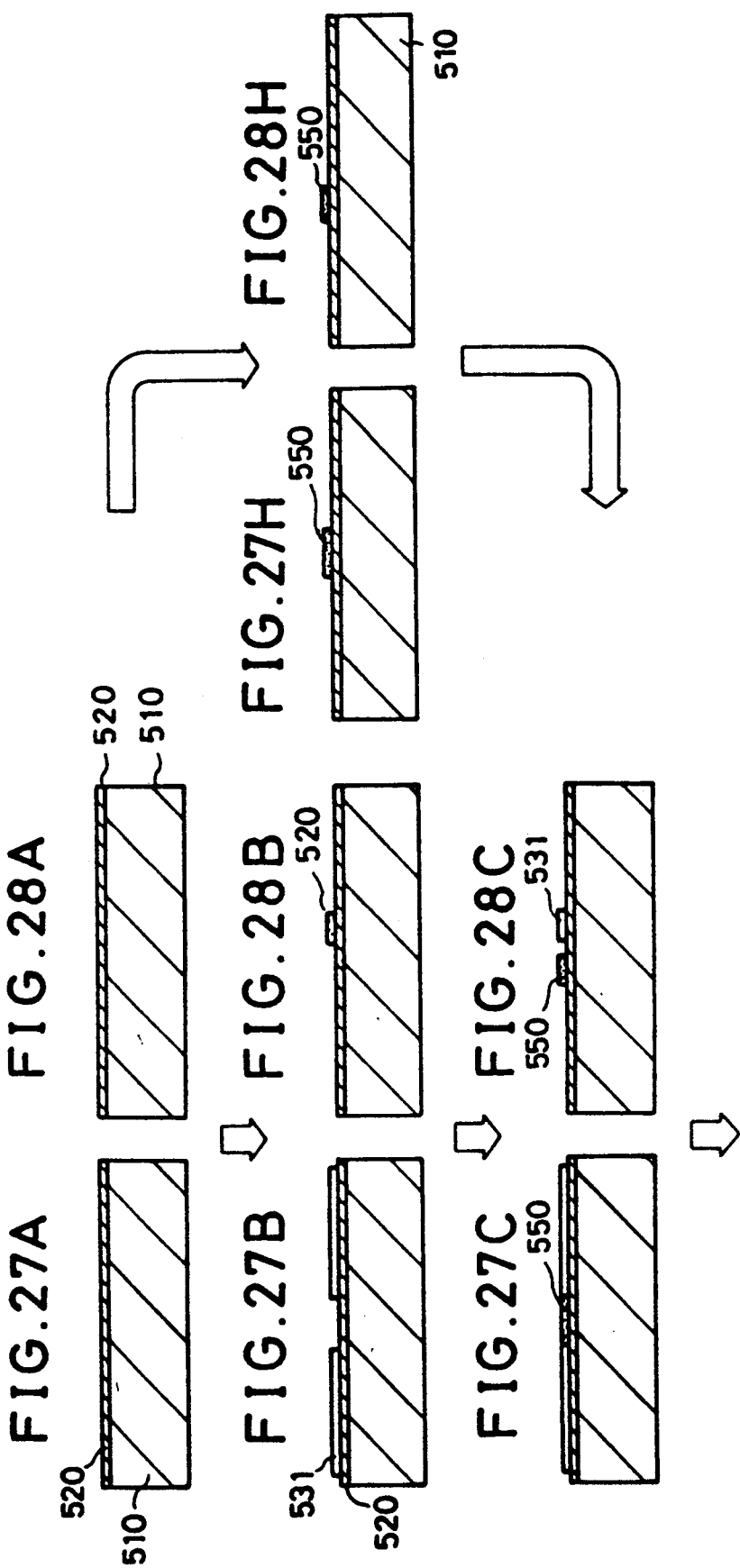

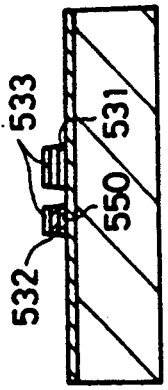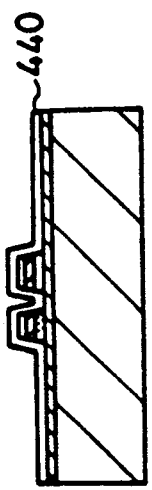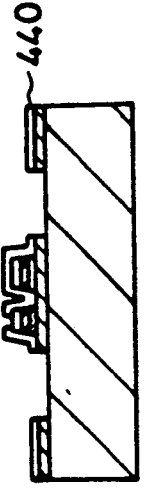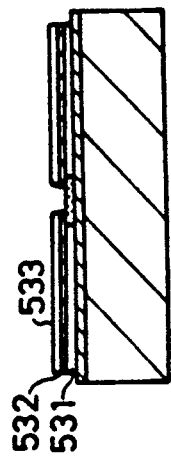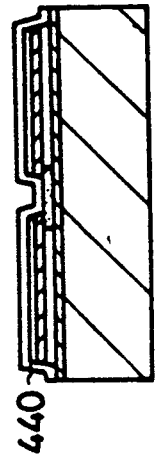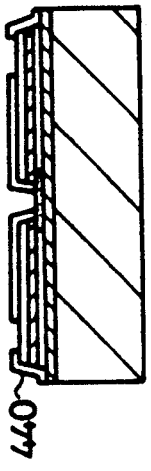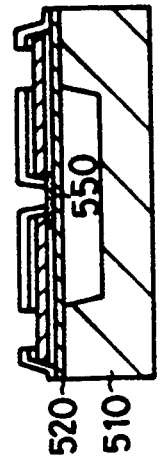

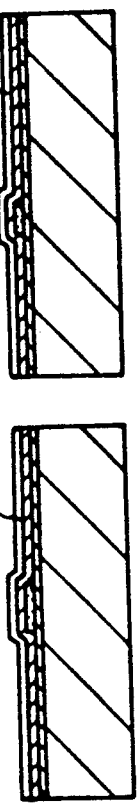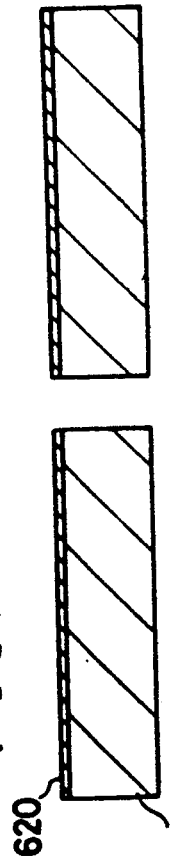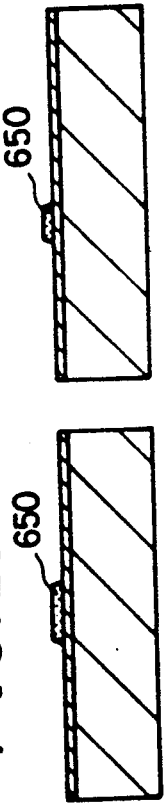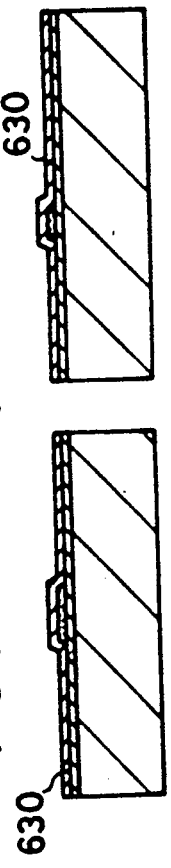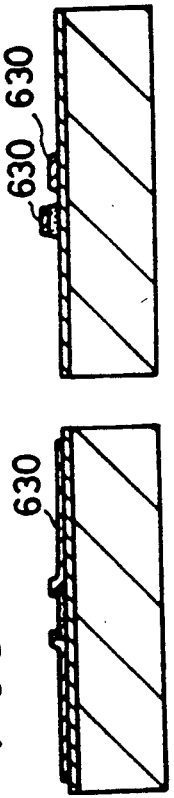

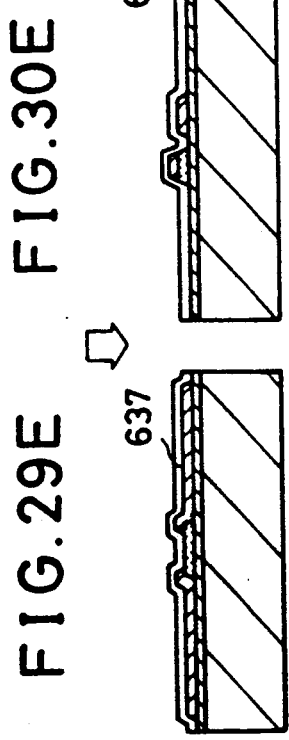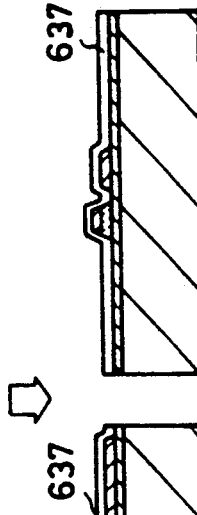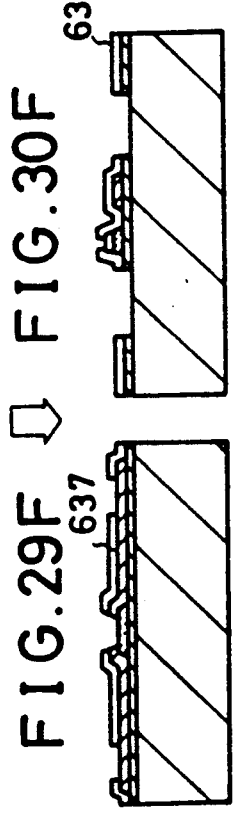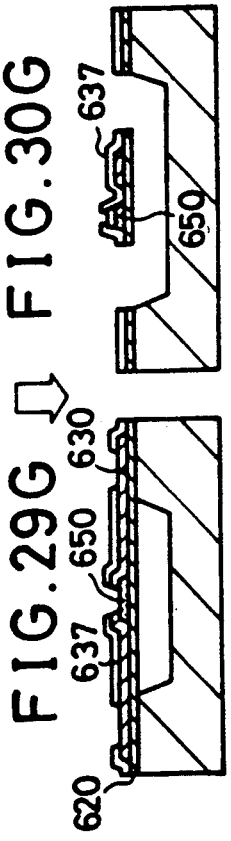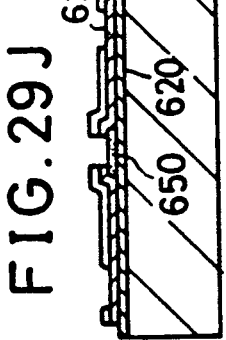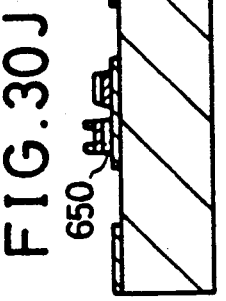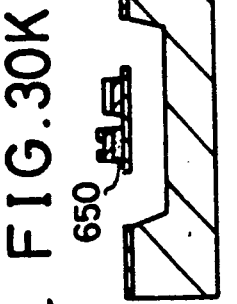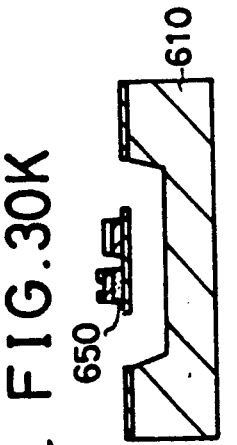

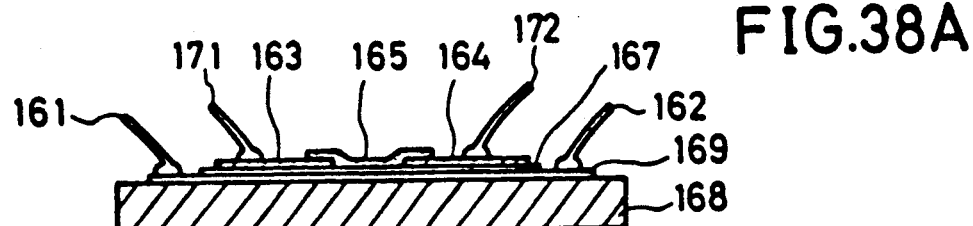
FIG.38A
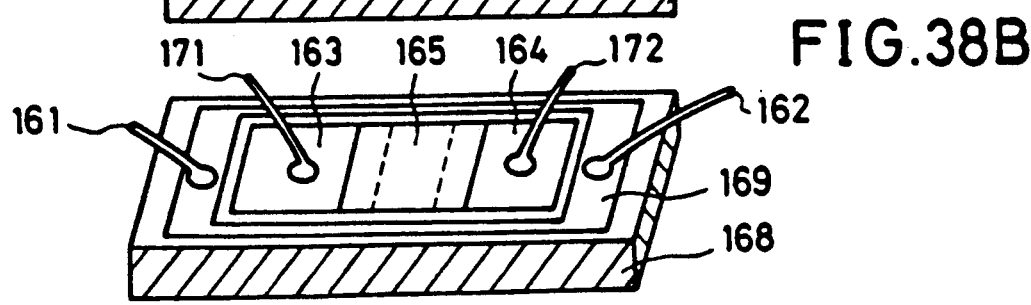
FIG.38B
FIG.38C
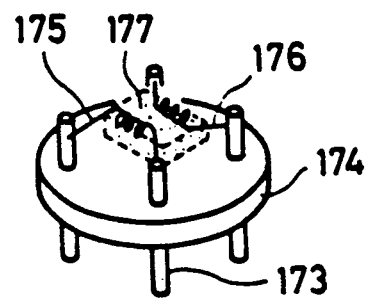
FIG.39
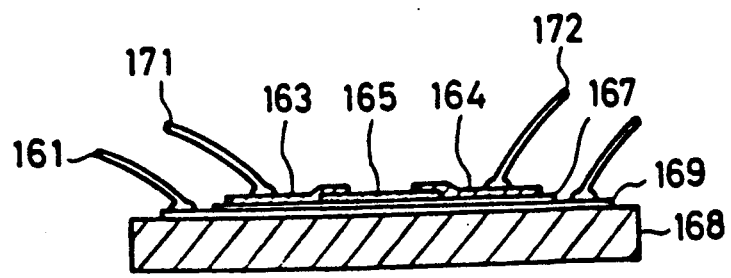

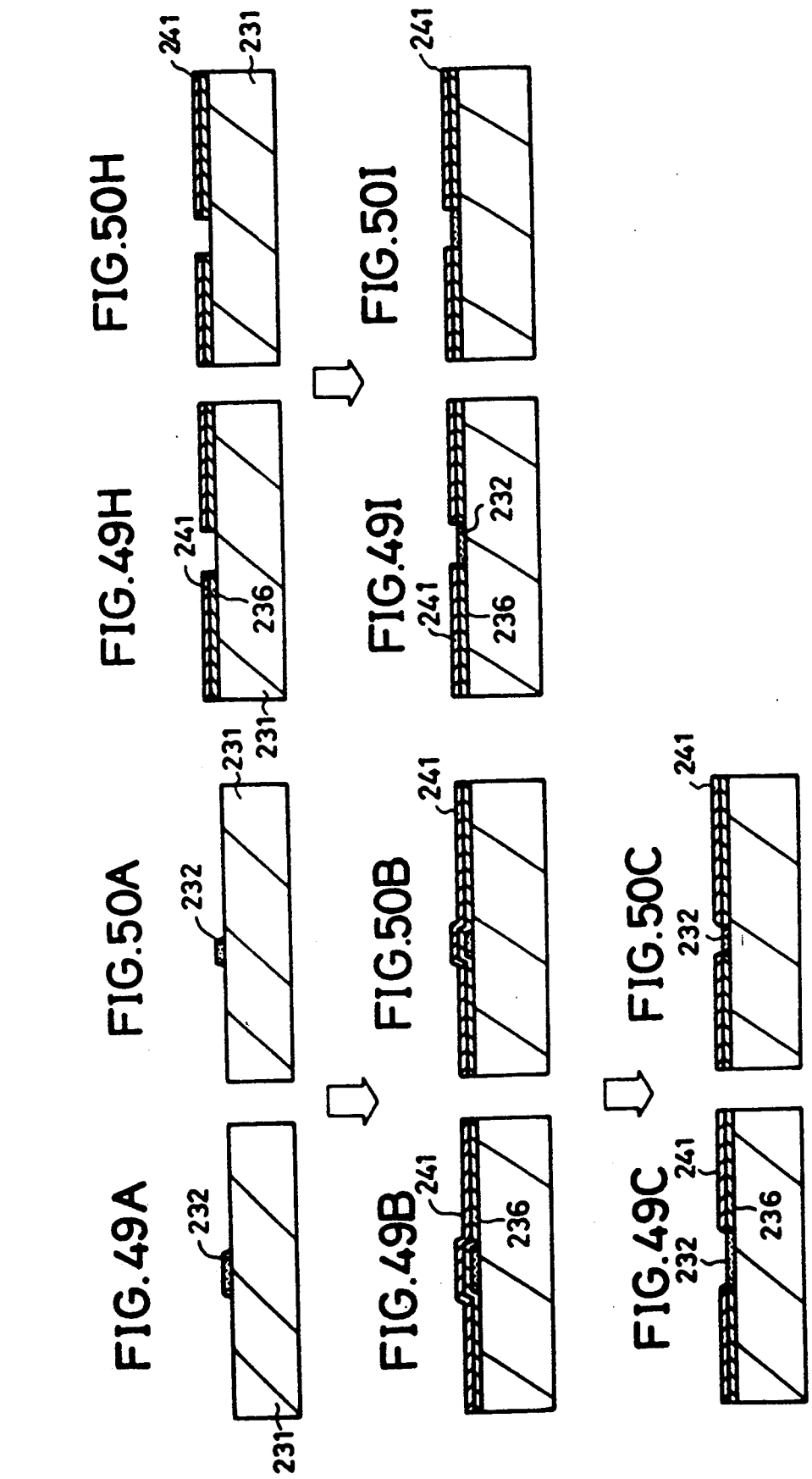

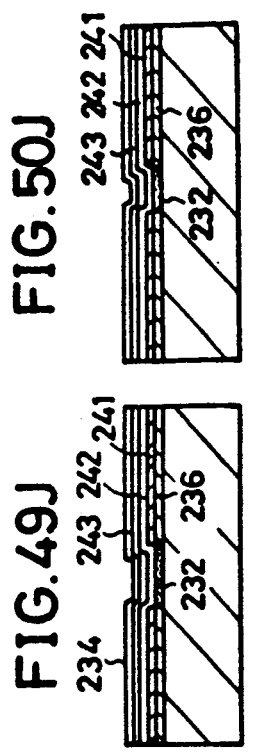
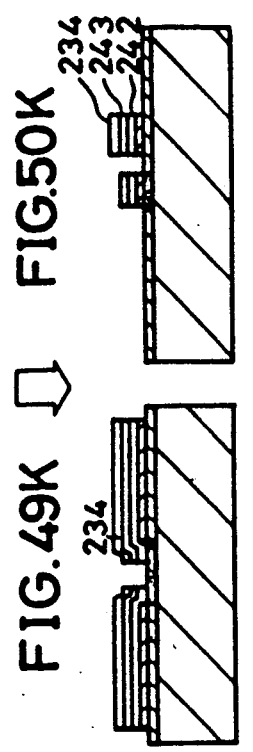
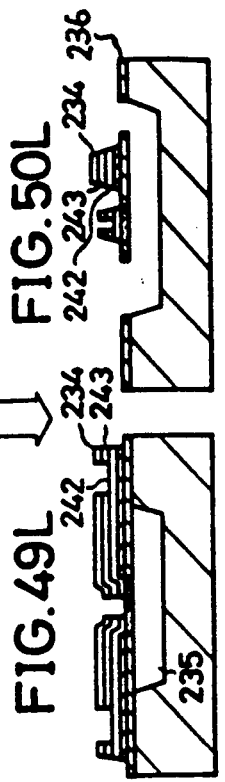
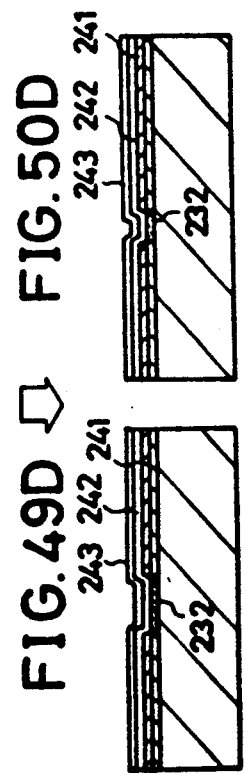
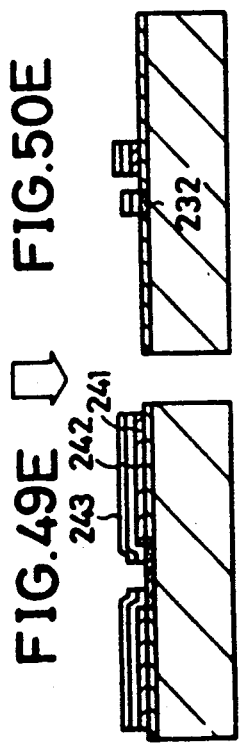
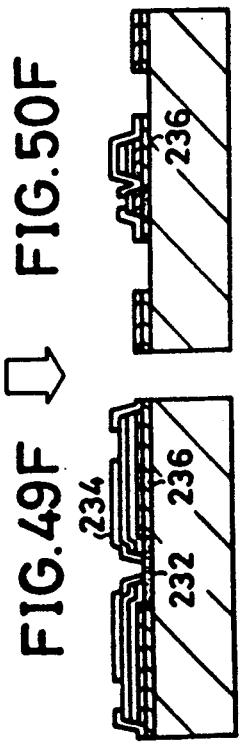
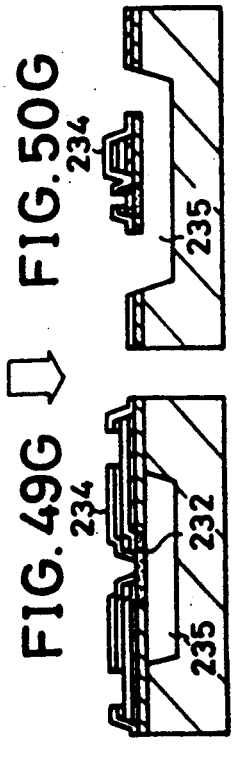

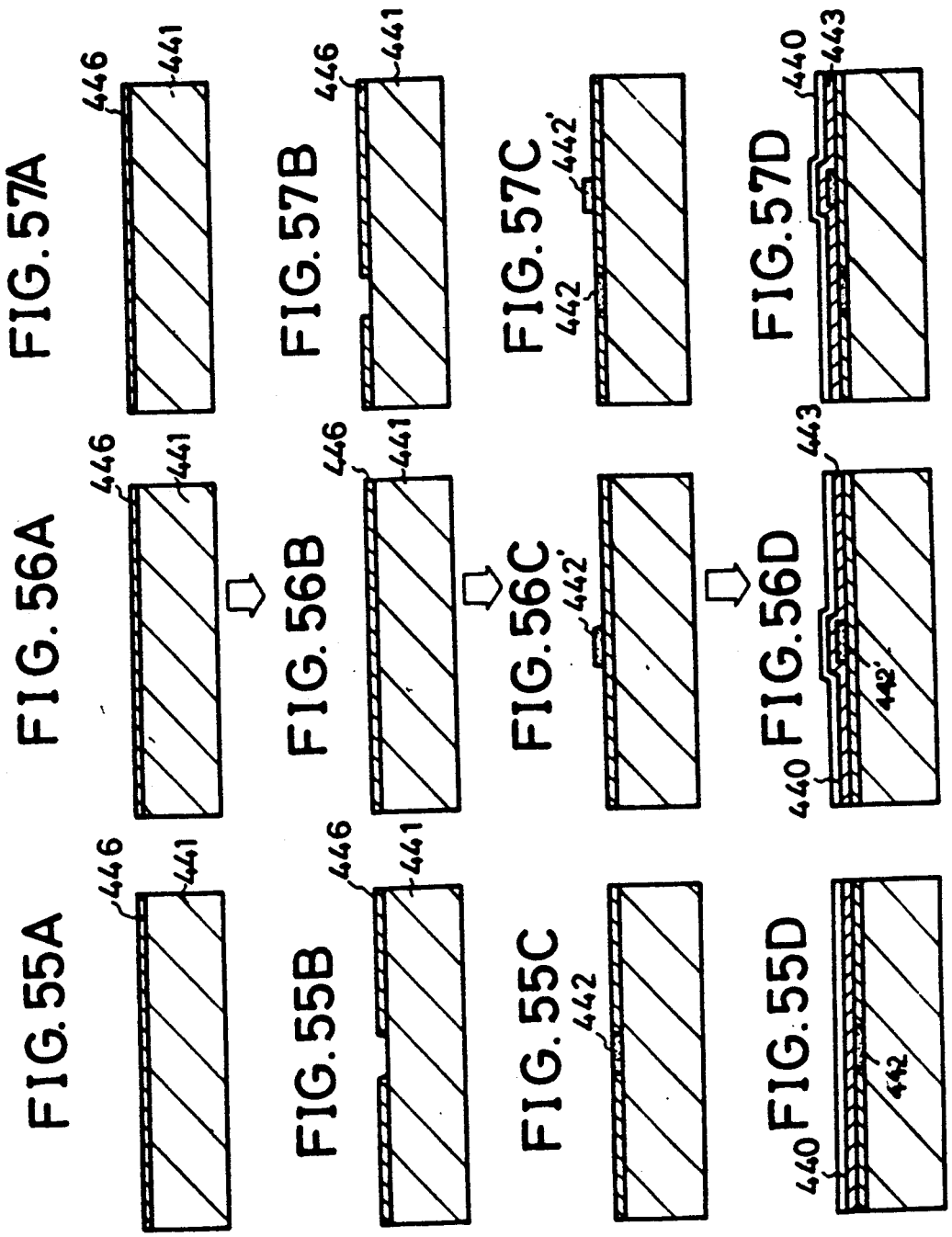

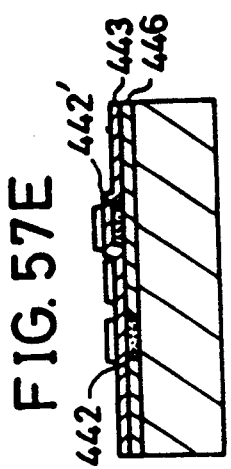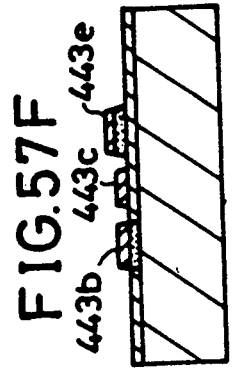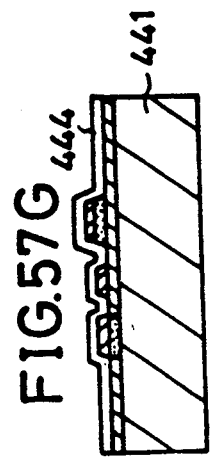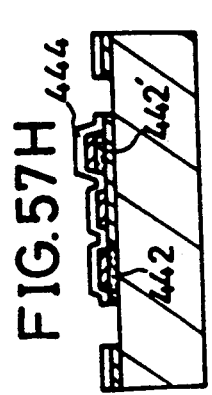
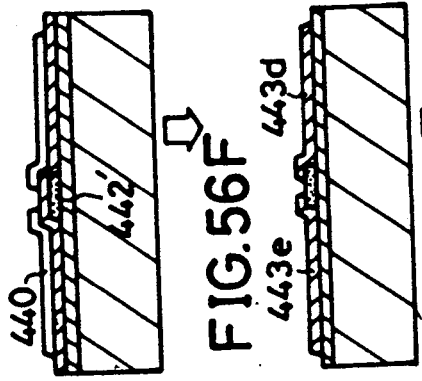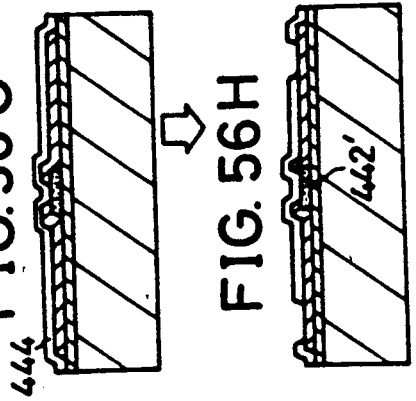
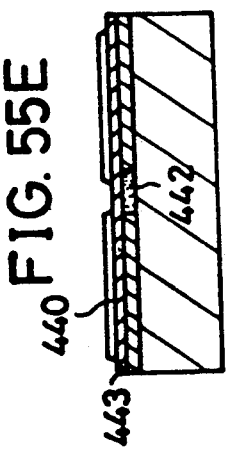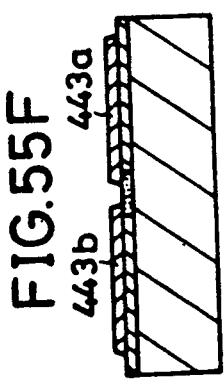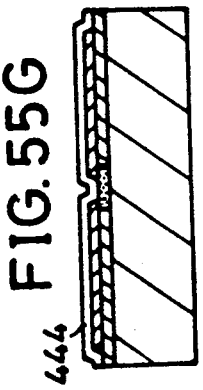

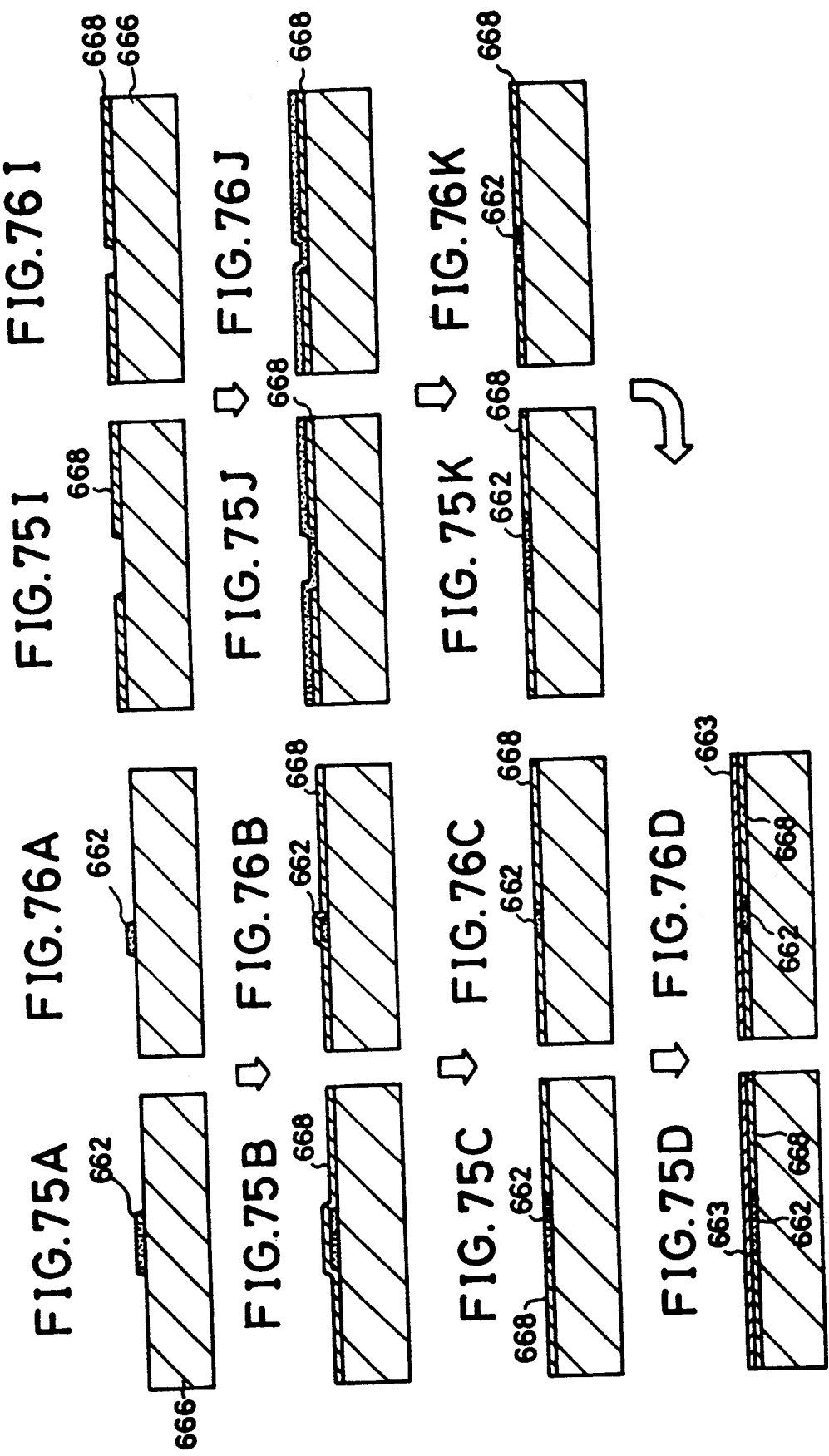

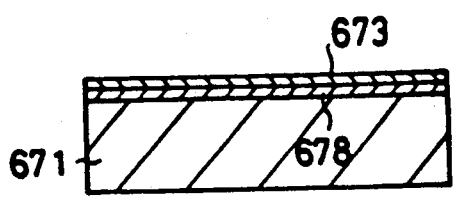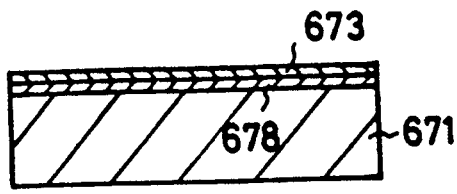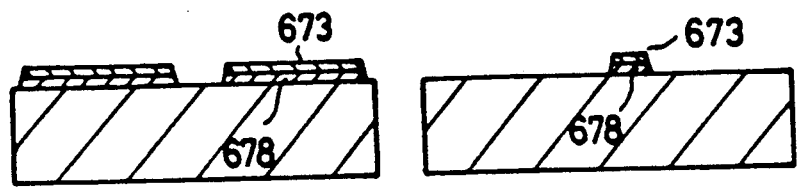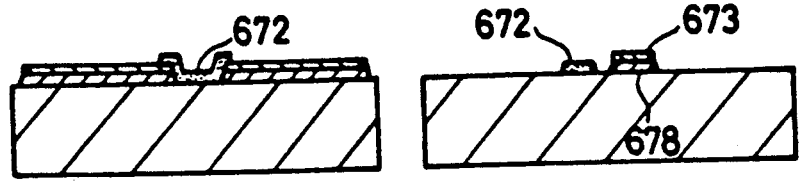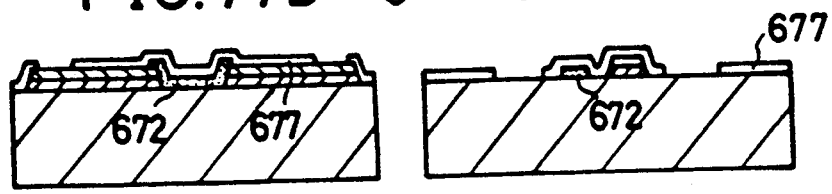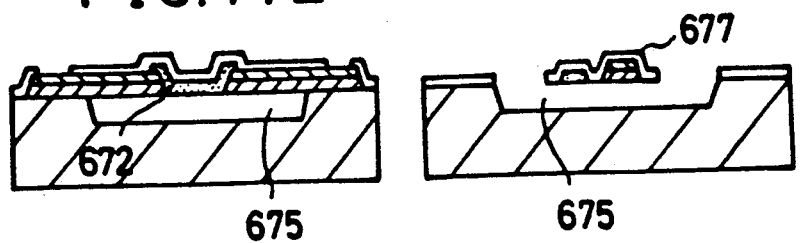

GAS DETECTING DEVICE

This is a division, of application Ser. No. 07/288,279, filed on Dec. 22, 1988 now U.S. Pat. No. 4,967,589.

BACKGROUND OF THE INVENTION

The present invention generally relates to a gas detecting device, and in particular to a gas detecting device suitable for a gas leak alarm designed to detect gas such as LP gas and commercialized gas.

A gas detecting device is proposed in the Japanese Laid-Open Patent Application No. 61-191953. The proposed gas detecting device (hereinafter referred to as a gas detector) is illustrated in FIG. 1A. The gas detector includes a substrate 11, an insulator layer 12, a pair of detection leads 13, an insulation coating layer 14, and a gas sensitive layer 15. The gas sensitive layer 15 is formed so as to partially overlie the insulator layer 12, the detection leads 13 and the insulation coating layer 14. The gas sensitive layer 15 is formed by depositing a metal oxide (ceramics) semiconductor material such as a tin dioxide, ($SnO_2$), ferrous oxide ($Fe_2O_3$), and zinc oxide (ZnO) by evaporation, sputtering, chemical vapor deposition, ion plating, and so on. The gas detecting operation is performed by applying heat to the gas sensitive layer 15 through a heater layer (not shown).

However, the proposed gas detector has disadvantages described below. The gas sensitive layer 15 is formed by depositing ceramics at low temperature. Therefore, volumetric shrinkage occurs in the gas sensitive layer 15. The ratio of shrinkage for the insulator layer 12, the detection leads 13 and the insulation coating layer 14 is smaller than that for the gas sensitive layer 15, even if those layers are grown at low temperatures.

In a case where the heater layer 13 detection lead is made of platinum (Pt), and the insulator layer 12 and the insulation coating layer 14 are made of silicon dioxide, the thermal expansion ratio for the detector lead is greater than those for the insulator layer 12 and the insulation coating layer 14, which are far greater than that for the gas sensitive layer 15. Thus, dislocation (or shear) is liable to occur in an interface between the gas sensitive layer 15 and the other layers. As a result, as shown in FIG. 1B, the gas sensitive layer 15 is liable to come off the gas detector.

In addition, the gas sensitive layer 15 is formed in a great step portion formed by the detection leads 13 and the insulation coating layer 14. For this reason, as shown in FIG. 2, the gas sensitive layer 15 is made thin at portions P, and may be cracked. That is, the step coverage of the gas sensitive layer 15 is poor. The above event degrades gas detection characteristics.

SUMMARY OF THE INVENTION

It is therefore a general object of the present invention to provide a novel and useful gas detecting device in which the above-mentioned disadvantages are eliminated.

A more specific object of the present invention is to provide a gas detecting device in which a gas sensitive layer is fixedly secured to other layers, and is prevented from coming off the stacked layer.

Another object of the present invention is to provide a gas detecting device in which cracks are hard to occur in the gas sensitive layer.

The above objects of the present invention can be achieved by a gas detecting device comprising a substrate, an insulator layer formed on the substrate, a gas sensitive layer formed the insulator layer, a pair of detection leads formed on the insulator layer, the gas sensitive layer partially overlying the pair of detection leads a signal derived from the gas sensitive layer being sent to an external circuit through the pair of detection leads, a heater member arranged on the insulator layer in the vicinity of the gas sensitive layer; and an insulation coating layer formed on the pair of detection leads and the heater member, and partially overlying the gas sensitive layer so that the gas sensitive layer is put between the insulator layer and the insulation coating layer, and a portion of an upper surface of the gas sensitive layer is exposed to gas.

The above-mentioned objects can be also achieved by a gas detecting device comprising a substrate, an insulator layer formed on the substrate, a gas sensitive layer formed the insulator layer, a pair of detection leads formed on the insulator layer, the pair of detection leads partially overlying the gas sensitive layer, a signal derived from the gas sensitive layer being sent to an external circuit through the pair of detection leads, a heater member arranged on the insulator layer in the vicinity of the gas sensitive layer, and an insulation coating layer formed on the pair of detection leads and the heater member, a portion of an upper surface of the gas sensitive layer being exposed to gas through opposed end portions of the pair of the detection leads and the insulation coating layer.

The above-mentioned objects can be also achieved by a gas detecting device comprising a substrate, an insulator layer formed on the substrate, a gas sensitive layer buried in the insulator layer, a pair of detection leads formed on the insulator layer, the pair of detection leads partially overlying the gas sensitive layer, a signal derived from the gas sensitive layer being sent to an external circuit through the pair of detection leads, a heater member arranged on the insulator layer in the vicinity of the gas sensitive layer, and an insulation coating layer formed on the pair of detection leads and the heater member, a portion of an upper surface of the gas sensitive layer being exposed to gas through the pair of the detection leads.

The above-mentioned objects can be also achieved by a gas detecting device comprising a substrate, an insulator layer formed on the substrate, a gas sensitive layer buried in the insulator layer, a pair of detection leads formed on the insulator layer, the pair of detection leads partially overlying the gas sensitive layer, a signal derived from the gas sensitive layer being sent to an external circuit through the pair of detection leads, a heater member arranged on the insulator layer in the vicinity of the gas sensitive layer, and an insulation coating layer formed on the pair of detection leads and the heater member, a portion of an upper surface of the gas sensitive layer being exposed to gas through the pair of the detection leads.

The above-mentioned objects can be also achieved by a gas detecting device comprising, a substrate having a cavity, an insulator layer formed across the cavity formed in the substrate, a gas sensitive layer buried in the insulator layer, a pair of detection leads formed on the insulator layer, a signal derived from the gas sensitive layer being sent to an external circuit through the pair of detection leads, the pair of detection leads partially overlying the gas sensitive layer, and an insulation coating layer formed on the pair of detection leads and the entire surface of the gas sensitive layer, a bottom surface of the gas sensitive layer facing the cavity, being served with a gas sensitive surface.

Other objects, features and advantages of the present invention will become apparent from the following detailed description when read in conjunction with the accompanying drawings.

BRIEF DESCRIPTION OF THE DRAWINGS

FIGS. 6A through 6I are cross sectional views with respect to the line IV—IV shown in FIG. 3, which are observed at different steps of a method for producing the embodiment of FIG. 3;

FIGS. 7A through 7I are cross sectional views with respect to the line V—V shown in FIG. 3, which are observed at different steps of a method for producing the embodiment of FIG. 3;

FIGS. 25A through 25L and FIGS. 26A through 26L are cross sectional views observed at different steps of a method for producing the gas detector shown in FIGS. 22 and 23;

FIGS. 27A through 27H and FIGS. 28A through 28H are cross sectional views observed at different steps of a method for producing an embodiment of the present invention;

FIGS. 29A through 29K and FIGS. 30A through 30K are cross sectional views observed at different steps of a method for producing an embodiment of the present invention;

FIGS 38A through 38C and FIG. 39 are views of embodiments of the present invention having features found by the experimental results illustrated in FIGS. 40 through 42;

FIGS. 49A through 49L are cross sectional views with respect to the line P—P' shown in FIG. 46, which are observed at different steps of a process for producing the gas detector of FIG. 46;

FIGS. 50A through 50L are cross sectional views with respect to the line Q—Q' shown in FIG. 46, which are observed at different steps of a process for producing the gas detector of FIG. 46;

FIGS. 55A through 55H are cross sectional views with respect to the line R—R', which are observed at different steps for producing the gas detector shown in FIG. 51;

FIGS. 56A through 56H are cross sectional views with respect to the line S—S', which are observed at different steps for producing the gas detector shown in FIG. 51;

FIGS. 57A through 57H are cross sectional views with respect to the line T—T', observed at different steps for producing the gas detector shown in FIG. 51;

FIGS. 75A through 75K are cross sectional views with respect to the line R—R' shown in FIG. 71, which are observed at different steps of a process for producing the gas detector shown in FIG. 71;

FIGS. 76A through 76K are cross sectional views with respect to the line S—S' shown in FIG. 71, which are observed at different steps of a process for producing the gas detector shown in FIG. 71;

FIGS. 77A through 77E are cross sectional views with respect to the line R—R' shown in FIG. 71, observed at different steps of another process for producing the gas detector shown in FIG. 71;

FIGS. 78A through 78E are cross sectional views with respect to the line S—S' shown in FIG. 71, which are observed at different steps of a process for producing the gas detector shown in FIG. 71;

DETAILED DESCRIPTION

Figure 3:
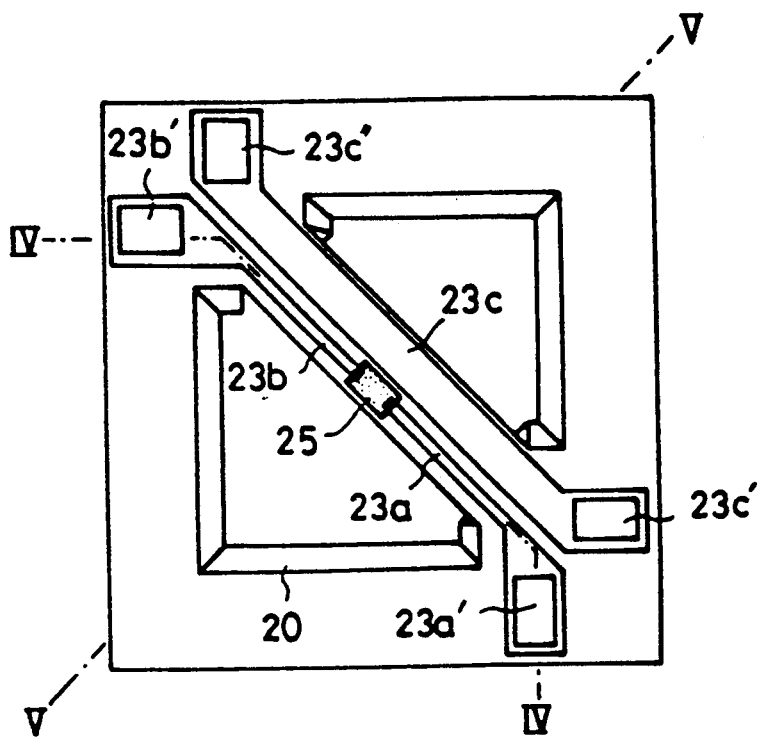
FIG. 3 is a plan view of a preferred embodiment of the present invention.
Figure 4:
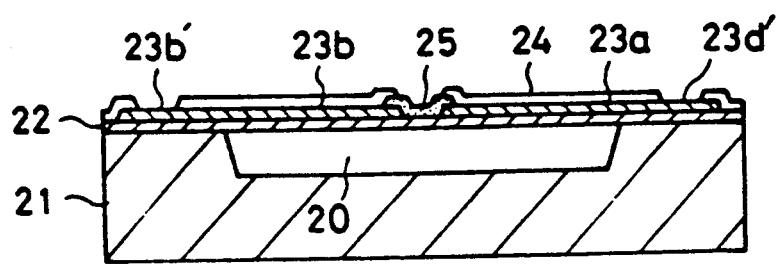
FIG. 4 is a cross sectional view taken along a line IV—IV shown in FIG. 3.
Figure 5:
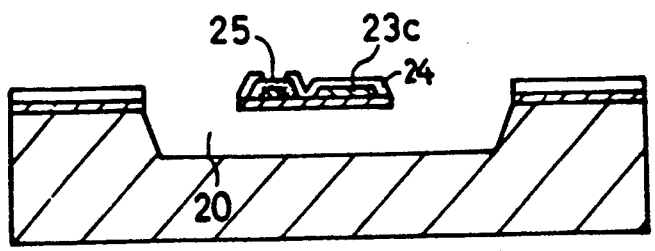
FIG. 5 is a cross sectional view taken along a line V—V shown in FIG. 3.

A description is given of an embodiment of the present invention with reference to FIGS. 3 through 5.

Referring to FIGS. 3 through 5, a gas detector of the embodiment comprises a heat-resistant substrate 21 made of silicon, a cavity (or groove) 20, an insulator layer 22, a pair of detection leads 23a and 23b, bonding pads 23a', 23b', 23c' and 23c'', a heater lead 13c, an insulation coating layer 24, and a gas sensitive layer 25. The insulator layer 22 is formed across the cavity 20 and connects corner portions of the substrate 21 on a diagonal line. This structure is of a bridge type. The detection leads 23a and 23b formed on the insulator layer 22 are used for sending a gas detection signal to an external circuit (not shown). End portions of the detection leads 23a and 23b are opposite to each other. The detection leads 23a and 23b include the bonding pads 23a' and 23b', respectively, which are exposed through respective openings formed in the insulation coating layer 24. The gas sensitive layer 25 is formed so as to partially overlie the detection leads 23a and 23b, and the insulation layer 22. The heater layer 23c is arranged on the insulator layer 22 along the detection leads 23a and 23b. Both the ends of the heater layer 23c include the bonding pads 23c' and 23c'', which are exposed through respective openings formed in the insulation coating layer 24.

It is preferable to utilize the (110) surface of silicon as the silicon substrate 21. In place of silicon, the heat-resistant substrate 21 may be made of aluminum, copper, nickel chromium, stainless or glass. The insulator layer 22 is made of silicon dioxide ($SiO_2$), alumina ($Al_2O_3$), silicon nitride ($Si_3N_4$), tantalum oxide ($TaO_5$), and so on. The insulation coating layer 24 is made of one of the above-mentioned materials for the insulator layer 22. For example, the insulation coating layer 24 may be made of a material identical to that for the insulator layer 22. Each of the detection leads 23a, 23b and the heater lead 23c can be made of gold (Au), platinum (Pt), palladium (Pd), irridium (Ir), rhodium (Rh), nickel chromium (NiCr), tantalum nitride ($Ta_2N$), silicon carbon (SiC), kanthal or the like. Hereinafter, the detection leads 23a, 23b including the bonding pads 23a', 23b', 23c', and 23c'', and the heater lead 23c is referred to as "a lead/heater layer" 23 as a whole.

It is to be noted that as can be clearly seen from FIGS. 4 and 5, the insulation coating layer 24 is provided so as to overlie and press end portions of the gas sensitive layer 25. Therefore, the gas sensitive layer 25 is put between the insulator layer 22 and the insulation coating layer 24. This is an essential feature of the embodiment. Since the lead/heater layer 23 and the insulator layer 22 have weak adhesion to the gas sensitive layer 25. Therefore, the presence of the insulation coating layer 24 is effective in preventing the gas sensitive layer 25 from coming off the device. Particularly, it becomes possible for the lead/heater layer 23c to be constructed by a single layer of a material which is hard to be oxidized and which does not have strong adhesion to the layers 22, 24 and 25, such as gold (Au), platinum (Pt), palladium (Pd), iridium (Ir) or rhodium (Rh). Alternatively, the lead/heater layer 23 may be constructed by a multilayer structure, in which the above-mentioned single resistor layer is sandwiched between adhesion reinforcement layers each made of nickel (N), tungsten (W), molybdenum (Mo), chromium (Cr), titanium (Ti), or the like.

In the above-mentioned multilayer structure, an alloy such as Au-Cr and Pt-Ni may be produced for a long term. Such an alloy functions to change resistance in the lead/heater layer 23 and decrease the melting point thereof. This degrades the accuracy in gas detection. For this reason, it is preferable to constitute the lead/heater layer 23 with a single layer. Of course, the adhesion reinforcement layers may be used in the embodiment. It should be appreciated that the gas sensitive layer 25 is put between the insulator layer 22 and the insulation coating layer 24.

A description is given of a method for producing the gas detector shown in FIGS. 3 through 5 with reference to FIGS. 6A through 6I, and FIGS. 6A through 7I. FIGS. 6A through 6I are cross sectional views taken along the line IV—IV shown in FIG. 3. FIGS. 7A through 7I are views taken along the line V-V shown in FIG. 3. In the method described below, the lead/heater layer 23 has the multilayer structure.

Referring to FIGS. 6A and 7A, a silicon dioxide layer 120 having a thickness of 0.2-2 μm is formed on a silicon substrate 110. Then, conductive layers 131, 132 and 133 are deposited on the silicon dioxide layer 120 in this order A lead/heater layer 130 comprising detection layers and heater layer, is made up of the layers 131, 132 and 133. The layers 131 and 133 function as adhesion reinforcement layers. Each of the layers 131 and 133 is 0.1-2 μm thick. For example, the layer 131 and 133 are made of molybdenum, and the layers 132 is made of platinum. The layers 131, 132 and 133 are formed by evaporation, sputtering, chemical vapor deposition, ion plating or the like. Then, an etching resist layer 140 of silicon dioxide is deposited to a thickness of 0.1-2 μm.

Referring to FIGS. 6B and 7B, a photoresist is provided on the etching resist layer 140, and is then patterned. Subsequently, the etching resist layer 140 is etched by a buffer hydrofluoric acid (HF+NH₂F) liquid. Then the layers 131, 132 and 133 are etched by argon sputter etching in which etching is carried out on the basis of a difference in sputtering yield between the layers 131, 132 and 133. Thereby, the structure shown in FIGS. 6C and 7C is obtained.

Then as shown in FIGS. 6D and 7D, the layer 133 of molybdenum is partially eliminated in order to establish a connection between detection leads of platinum and a gas sensitive layer of tin dioxide ($SnO_2$). This can be done by depositing and then patterning a photoresist and then patterning the layer 133 by a rare nitric acid liquid so that portions of the layer 133 corresponding to positions of bonding pads and gas sensitive layer are removed.

Thereafter, as shown in FIGS. 6E and 7E, a layer of tin dioxide is formed on the entire surface of the substrate 110. Then a photoresist is deposited and patterned. Then the tin dioxide layer is patterned by plasma etching so that a patterned gas sensitive layer 150 can be obtained.

Then, as shown in FIGS. 6F and 7F, an insulation coating layer 141 made of silicon dioxide is deposited to a thickness of 0.1-2 μm, and is then patterned. Then, holes above the gas sensitive layer 150, and openings or windows for bonding pads, and an etching window used for forming a cavity 100 are formed in the insulation coating layer 141. This is done by using a buffer hydrofluoric acid liquid.

Referring to FIGS. 6G and 7G, by using a sodium hydroxide liquid, the silicon substrate 110 is etched through the etching window so that the cavity 100 having a depth of 10-200 μm is formed therein.

The steps shown in FIGS. 6A through 6C and FIGS. 7A through 7C may be substituted with steps shown in FIGS. 6H and 6I and FIGS. 7H and 7I. As shown in these figures, after forming the layers 131, 132 and 133, a photoresist is formed and is then patterned. Then the layers 131-133 are plasma-etched.

Figure 8:
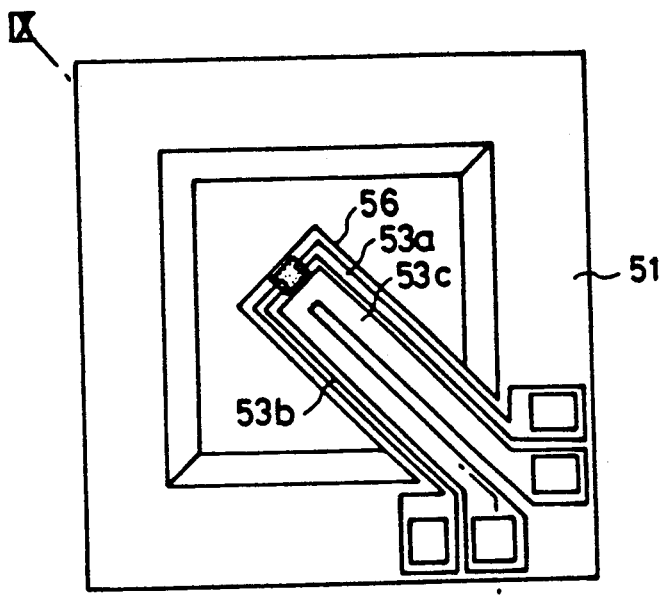
FIG. 8 is a plan view of another embodiment of the present invention.
Figure 9:
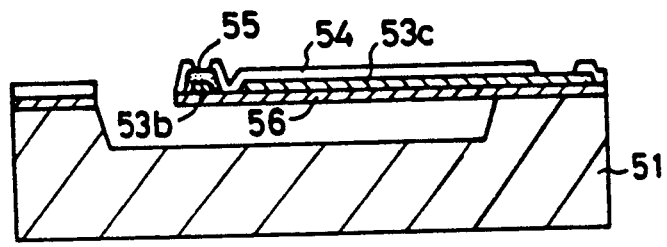
FIG. 9 is a cross sectional view taken along a line IX—IX shown in FIG. 8.

A description is given of another preferred embodiment of the present invention with reference to FIGS. 8 and 9. The illustrated gas detector is of a cantilever type. An end of an insulator layer 56 is fixed to a corner portion of a silicon substrate 51, and the other end thereof is a free end. On the insulator layer 56, there are formed a heater lead 53c, detection leads 53a and 53b, and a gas sensitive layer 55. An insulation coating layer 54 is formed as shown in FIG. 9. It is noted that the gas sensitive layer 55 is put between the insulator layer 56 and the insulation coating layer 54. Therefore, the embodiment of FIGS. 8 and 9 has the advantages identical to those provided by the embodiment described previously. The heater lead 53c is arranged so as to be surrounded by the detection leads 53a and 53b. Alternatively, it is possible to arrange the detection leads 53a and 53b inside the arrangement of the heater lead 53c.

Figure 10:
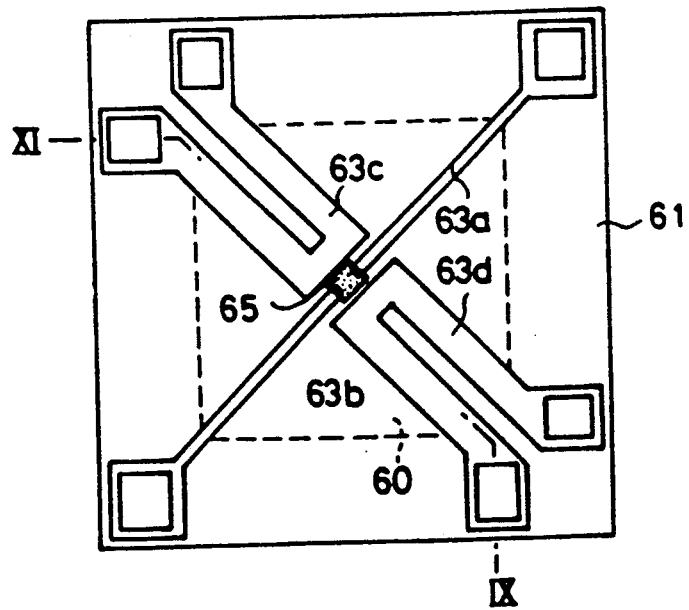
FIG. 10 is a plan view of still another embodiment of the present invention.
Figure 11:
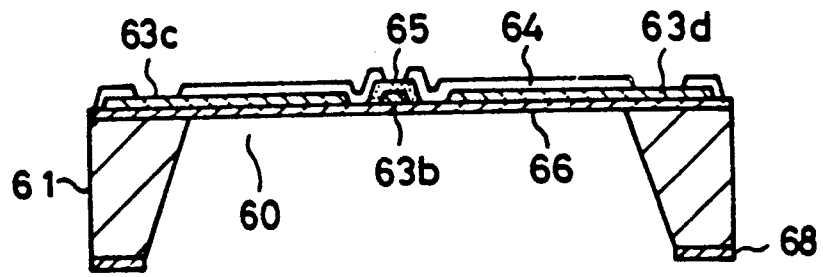
FIG. 11 is a cross sectional view taken along a line XI—XI shown in FIG. 10.

FIGS. 10 and 11 show a still another embodiment of the present invention. This is of the diaphragm type. In the illustrated embodiment, a cavity or groove 60 is formed in a substrate 61 so as to penetrate the center portion of the substrate 61. The cavity 60 can be formed by etching from the bottom side of the substrate 61. In this case, it is necessary for the substrate 61 to be made of a material to which etching is possible, and at the same time, it is possible for a pattern layer 68 deposited on the bottom surface of the substrate 61 to be made of a material which is not etched by the same etchant. That is, the pattern layer 68 is made of a material by which selective etching can be enabled. For example, the substrate 61 is made of silicon, and an insulator layer 66 and an insulation coating layer 64 are made of silicon dioxide, and the pattern layer 68 is made of silicon dioxide. In this case, the patterning for the pattern layer 68 can be performed at the same time as the layers 64 and 66 are patterned. In FIGS. 10 and 11, it is noted that the detection leads 63a and 63b are formed so as to cross the heater leads 63c and 63d.

Figure 12:
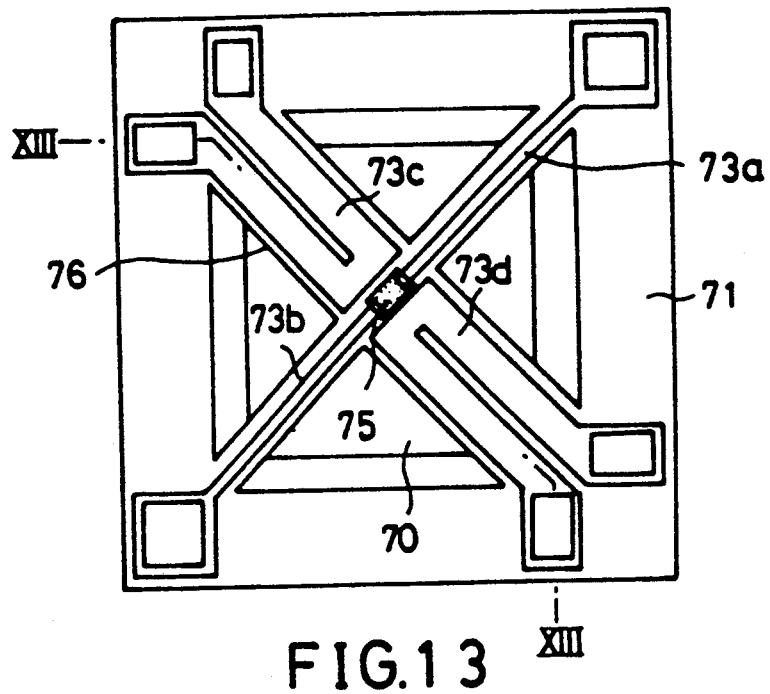
FIG. 12 is a plan view of a further embodiment of the present invention.
Figure 13:
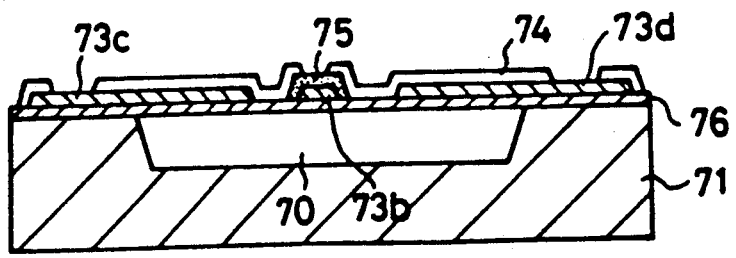
FIG. 13 is a cross sectional view taken along a line XIII—XIII shown in FIG. 12.

FIGS. 12 and 13 show a variation of the embodiment of FIGS. 10 and 11. As shown in these figures, an insulator layer 76 has a cross shape. On the insulator layer 76, there are arranged detection leads 73a and 73b and heater leads 73c and 73d. A cavity 70 is formed in a silicon substrate 71 by etching through from a top surface thereof. The cavity 70 does not penetrate the silicon substrate 71. An insulation coating layer 74 is formed so as to overlie and press end portions of the gas sensitive layer 75.

Figure 14:
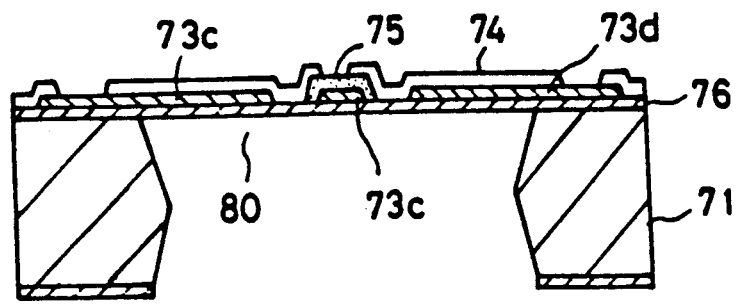
FIG. 14 is a cross sectional view of a still further embodiment of the present invention.
Figure 15:
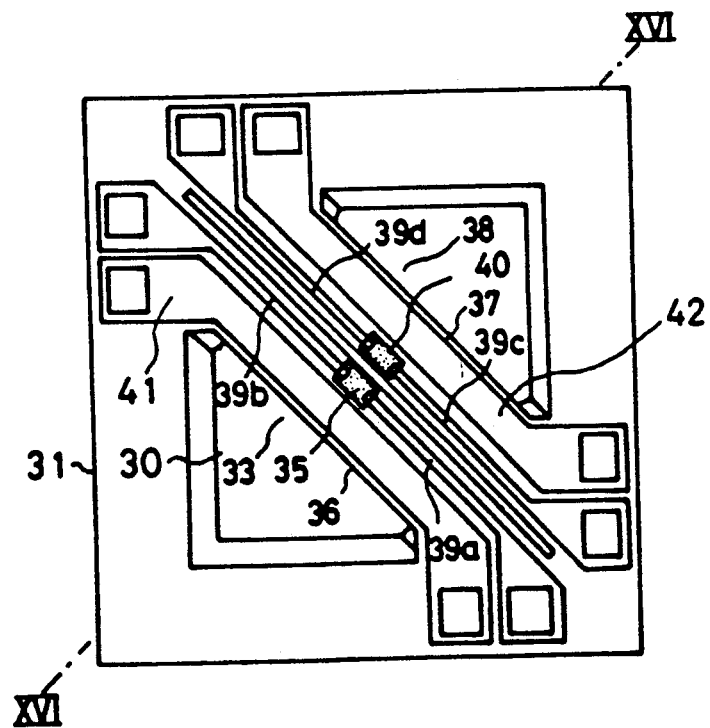
FIG. 15 is a plan view of a still further embodiment of the present invention.

FIGS. 14 and 15 show a variation of the embodiment of FIGS. 12 and 13. In this embodiment, a cavity 80 is formed by forming the aforementioned opening 70 from the upper side of the silicon substrate 71, and then forming a cavity from the bottom side thereof so as to connect the cavity 70. Thereby, the cavity 80 is formed so as to penetrate the silicon substrate 71.

Figure 16:
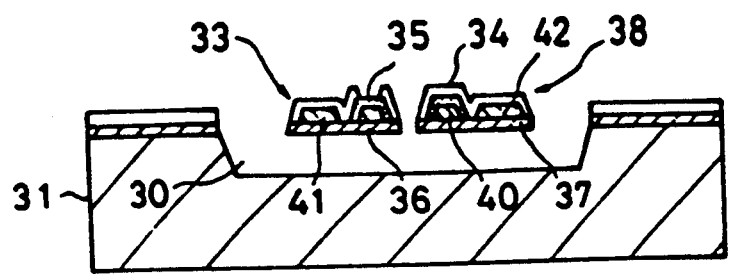
FIG. 16 is a cross sectional view taken along a line XVI—XVI shown in FIG. 15.

A description is given of a further embodiment of the present invention with reference to FIGS. 15 and 16. Referring to FIGS. 15 and 16, a gas detection element 33 comprising a gas sensitive layer 35, and a temperature compensation element 38 comprising a temperature sensitive layer 40 are formed on a single silicon substrate 31. The gas sensitive layer 35 is formed on an insulator layer 36. Detection leads 39a and 39b formed on the insulator layer 36 are connected to the gas sensitive layer 35. An insulation coating layer 38 is formed so as to overlie and press end portions of the gas sensitive layer 35. Heater layers 41 and 42 are formed on the insulator layer 36. On the other hand, the temperature sensitive layer 40 is formed on an insulator layer 37. Leads 39c and 39d formed on the insulator layer 37 are connected to the temperature sensitive layer 40. The temperature sensitive layer 40 may be formed by the same material and the same step as the gas sensitive layer 35. The entire surfaces of the temperature sensitive layer 40 and the heater layer 42 are covered with the insulation coating layer 34. With this structure, the temperature sensitive layer 40 does not become sensitive to gas, and is sensitive to temperature around it. As a result, the temperature sensitive layer 40 functions as a temperature compensation element. A signal derived from the temperature sensitive element is sent to an external circuit (not shown) through the leads 39c and 39d, and is used for controlling the power supplied to the heater leads 41 and 42. A cavity 30 is continuous under the insulation layers 36 and 37. The consinuous cavity 30 results in an advantage in which temperature around the detection layer 35 is almost the same as that around the temperature sensitive layer 40. Alternatively, two separate cavities may be formed unter the insulation layers 36 and 37. In this case, an increased difference in temperature exists between the detection layer 35 and the temperature sensitive layer 40.

Figure 17A:
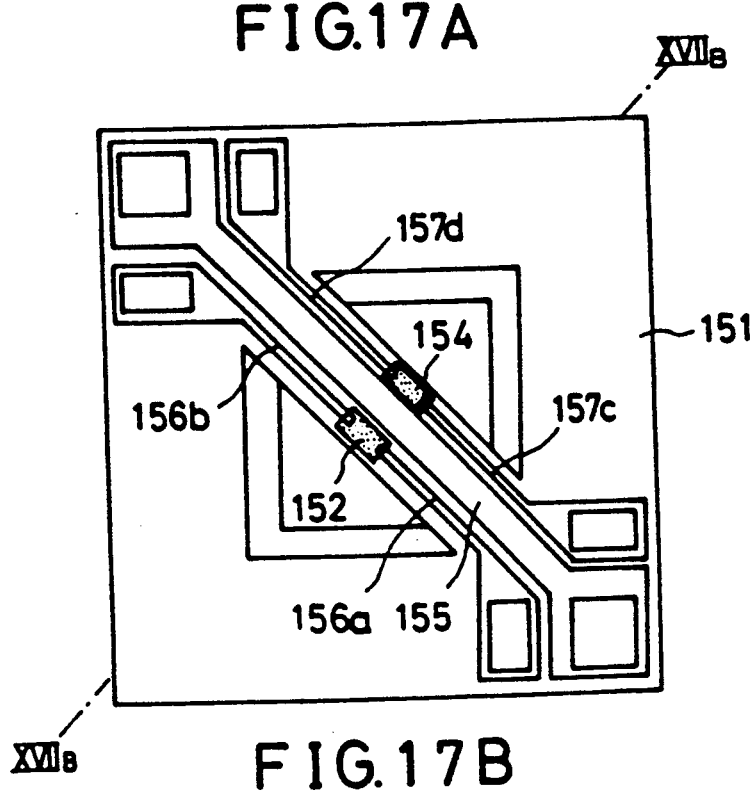
FIG. 17A is a plan view of a still further embodiment of the present invention.
Figure 17B:
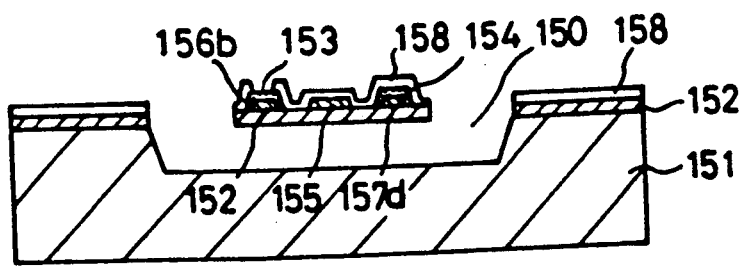
FIG. 17B is a cross sectional view taken along a line $XVII_B$—$XVII_B$ shown in FIG. 17A.

FIGS. 17A and 17B show a variation of the structure shown in FIG. 15. A cavity 150 is formed in a silicon substrate 151. An insulation layer 152 extends over two corner portions of the substrate 151. On the insulation layer 152, there are formed on a gas sensitive layer 156, a temperature sensitive layer 154, detection leads 156a and 156b, leads 157c and 157d, and an insulation coating layer 158. The insulation coating layer 158 is provided so as to overlie and press end portions of the gas sensitive layer 153 and cover the entire temperature sensitive layer 154 and the heater lead 155. It is noted that the embodiment of FIG. 15 has two heater leads 41 and 41, whereas the embodiment of FIGS. 17A and 17B employs one heater lead 155 interposed between the detection leads 156a, 156b and 157c and 157d. By the structure of FIGS. 17A and 17B, it becomes possible to reduce the power consumption of heater leads and set the leads 157a, 157b, 157c and 157d to the almost same temperature.

Figure 18:
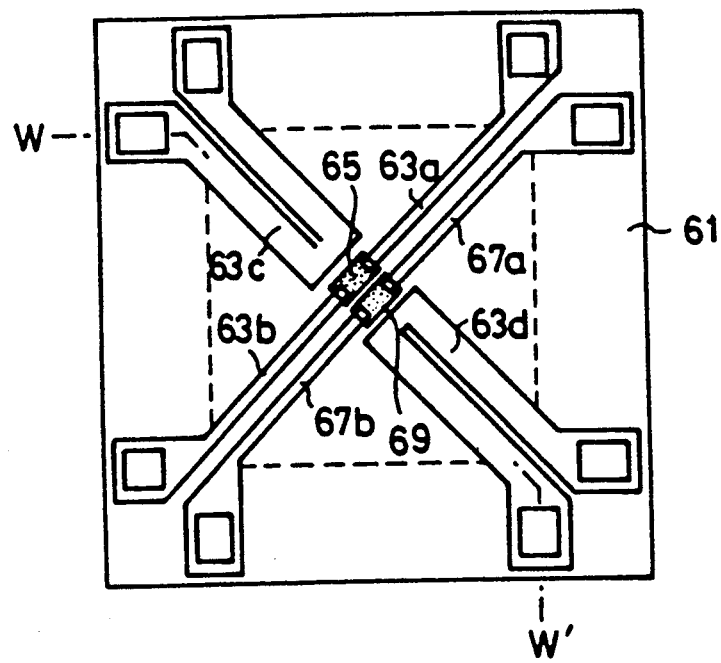
FIG. 18 is a plain view of a still further embodiment of the present invention.
Figure 19:
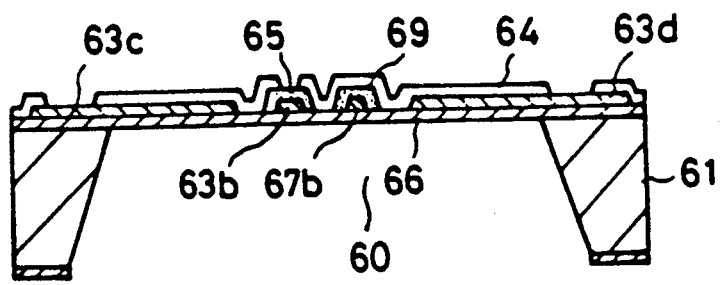
FIG. 19 is a cross sectional view taken along a line W—W' shown in FIG. 18.

FIGS. 18 and 19 illustrate a structure obtained by applying the temperature compensation function in FIGS. 15 and 16 to the embodiment shown in FIGS. 9 and 10. Referring to FIGS. 18 and 19, leads 67a and 67b connected to a temperature sensitive layer 69, are arranged on the insulator layer 66 along the detection leads 63a and 63b.

Figure 1A:
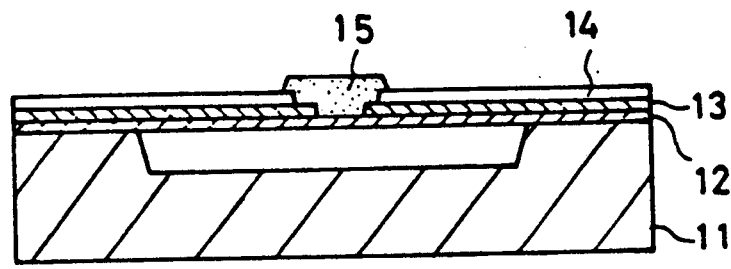
FIGS. 1A and 1B are cross sectional views of a conventional gas detector.
Figure 1B:
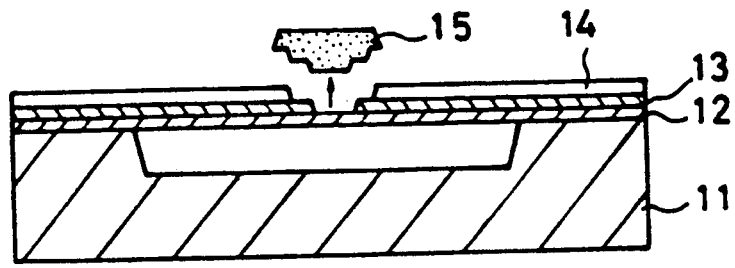
Figure 2:
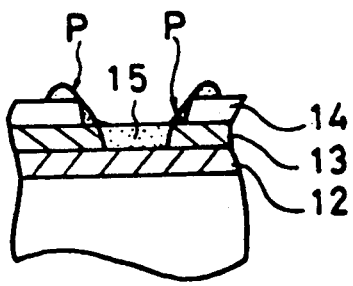
FIG. 2 is a view showing a part of the cross section of the conventional gas detector, which illustrate a problem thereof.
Figure 20A:
FIGS. 20A through 20C are cross sectional views for explaining problems encountered in the conventional gas detector.
Figure 20B:
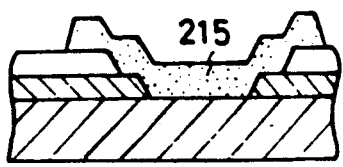
Figure 20C:
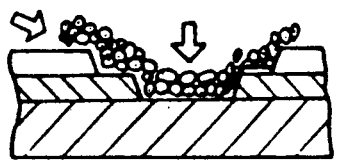

Now, the disadvantages of the prior art shown in FIGS. 1 and 2 are again described with reference to FIGS. 20A through 20C. As described previously in the section of the background of the invention, a gas sensitive layer 215 is formed on end portions of detection leads 213a and 213b formed on an end portion of an insulator layer 212, and an insulator layer 214. During the gas detection operation, the gas sensitive layer 215 is heated by a heater lead (not shown), and is therefore subjected to a temperature of 300°–400° C. As a result, as shown in FIG. 20C, the growth of crystal grains and the volumetric shrinkage occur in the gas sensitive layer 215. For this reason, the electrical connection between the gas sensitive layer 215 and detection leads 213a and 213b is degraded, and finally the gas sensitive layer 215 may come off the detection leads 213a and 213b and the insulator layer 214. The gas sensitive layer 215 is grown at a temperature considerably lower than the melting point thereof by evaporation, sputtering, chemical vapor deposition or ion plating. On the other hand, the insulator layers 212 and 214 are silicon dioxide, for example, and the detection leads 213a and 213b are made of molybdenum, platinum or the like. These materials have properties similar to a bulk thereof, and exhibit less volumetric shrinkage.

In order to overcome the above-mentioned disadvantage, in the aforementioned embodiments, the gas sensitive layer is formed so as to be partially pressed by the insulation coating layer. According to the present invention, another solution is proposed.

Figure 21A:
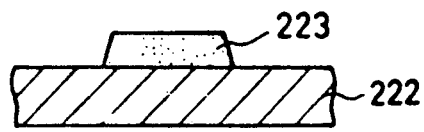
FIG. 21A through 21C are cross sectional views which illustrate an essential feature of the present invention.
Figure 21B:
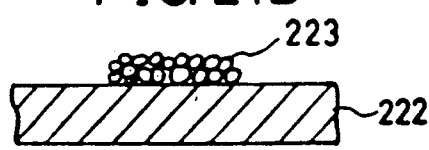
Figure 21C:
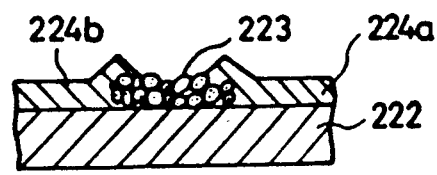

Referring to FIG. 21A, a gas sensitive layer 223 formed on an insulator layer 222 is patterned and is then sintered. The sintering is carried out in an air or an $O_2$ gas at a temperature of 400° to 1000° C. It is preferable to the gas sensitive layer 223 having a thickness of 0.05–2 μm in an air at 600° C. for 30 minutes to 3 hours. The gas sensitive layer 223 after this process is shown in FIG. 21B. Then detection leads 224a and 224b are formed so as to partially overlie the gas sensitive layer 223. Thereby the contact state between the gas sensitive layer 223 and the detection leads 224a and 224b can be improved. Further, when the gas sensitive layer 223 is heated during the gas detection, no shrinkage occurs because the gas sensitive layer 223 has been shrunk by sintering. Therefore, there is less change of properties of the gas sensitive layer 223 for a long term. Then, as shown in FIG. 21C, detection leads 224a and 224b are formed so as to partially overlie the gas sensitive layer 223. It is noted that the insulation coating layer 24 partially overlies the gas sensitive layer 25 (FIGS. 3 through 5), whereas the detection leads 224a and 224b partially overlie the gas sensitive layer 223.

Figure 22:
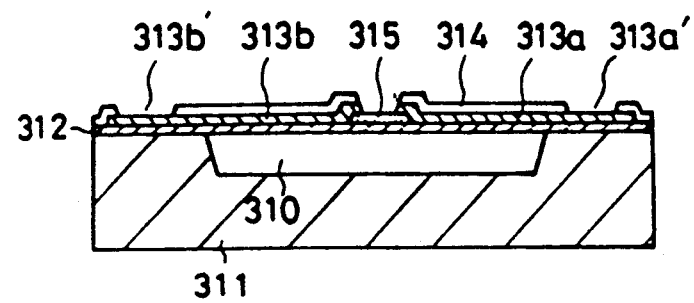
FIGS. 22 through 24 are cross sectional views of embodiments of the present invention which have the feature shown in FIG. 21C.
Figure 23:
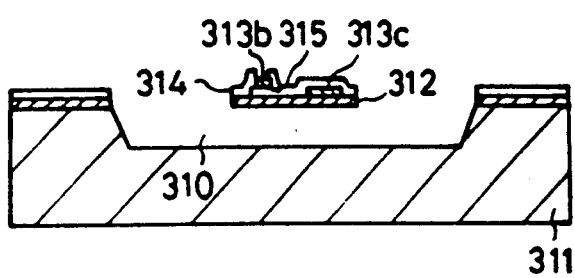

A detailed description is given of an embodiment of the type of FIG. 21C with reference to FIGS. 22 and 23. FIG. 22 shows a cross section of the embodiment having the same direction as that of the embodiment shown in FIG. 4. FIG. 23 shows a cross section of the embodiment having the same direction as that of the embodiment shown in FIG. 5. Referring to FIGS. 22 and 23, an insulator layer 312 is across a cavity 310 formed in a substrate 311 and connects two corner portions of the silicon substrate 311. A gas sensitive layer 315 is formed on the insulator layer 312. A pair of detection leads 313a and 313b are formed so as to overlie end portions of the gas sensitive layer 315. An insulation coating layer 314 is formed on the entire surface, and has holes. The upper surface of the gas sensitive layer 315 is exposed. Reference numerals 313a' and 313b' indicate bonding pad portions of the detection leads 313a and 313b, respectively.

Figure 24:
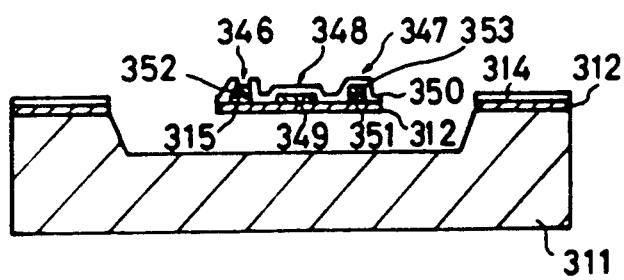

FIG. 24 is a variation obtained by applying the aforementioned temperature compensation to the structure shown in FIGS. 22 and 23. The cross section in FIG. 24 has the same direction as that shown in FIG. 17B. On a bridge portion of the insulator layer 314, there are formed a gas detection element 346, a temperature compensation element 347, a heater lead 349, and an insulation coating layer 350. A detection lead 352 is formed so as to partially overlie the gas sensitive layer 315. Likewise, a lead 353 is formed so as to partially overlie the temperature sensitive layer 351. The insulation coating layer 350 is formed as shown in FIG. 24. Alternatively, in the structures shown in FIGS. 22 through 24, cantilever structures may be employed.

A description is given of a method for producing the embodiment shown in FIGS. 22 and 23 with reference to FIGS. 25A through 25L and FIGS. 26A through 26L. Although each of the detection leads 313a and 313b is constituted by the single layer, the structure described below has a detection lead by a trilayer.

Referring to FIGS. 25A and 26A, an insulator layer 420 made of silicon dioxide is formed to a thickness of 0.2–2 μm. Then as shown in FIGS. 25B and 26B, a tin dioxide layer is deposited on the insulator layer 420, and is then patterned by photoetching so that a gas sensitive layer 450 is formed. Then the gas sensitive layer 450 is sintered.

Referring to FIGS. 25C and 26C, a molybdenum layer 431 served as an adhesion reinforcement layer is deposited to a thickness of 0.03–2 μm. Then a platinum layer 432 is deposited to a thickness of 0.05–2 μm. Then a molybdenum layer 433 served as an adhesion reinforcement layer is deposited to a thickness of 0.03–2 μm.

Thereafter, as shown in FIGS. 25D and 26D, a photoresist is deposited on the layer 433, and then the layers 431, 432 and 433 are patterned by plasma etching or sputter etching. References 432a and 432b indicate detection leads which have been sintered. It is noted that upper end portions of the gas sensitive layer 450 is formed so as to partially underlie the stacked layer made up of the layers 431–433. Then, as shown in FIGS. 25E and 26E, an insulation coating layer 440 of silicon dioxide is deposited to a thickness of 0.1–2 μm. Then as shown in FIGS. 25F and 26F, the insulation coating layer 440 is subjected to etching in which a buffer hydrofluoric acid liquid is used as an etchant so that an upper surface portion of the gas sensitive layer 450 is exposed and the layer 433 is partially exposed at positions 430a' and 430b' at which bonding pads to be formed. It is noted that ends of the insulation coating layer 440 overlie the gas sensitive layer 450. Subsequently, as shown in FIGS. 25G and 26G, the layer 433 is partially etched at the positions of the bonding pads by using a rare nitric acid liquid. Then, as shown in FIGS. 25H and 26H, the silicon substrate 410 is etched by an NaOH liquid through an etching window so that a cavity 400 having a depth of 10–200 μm is formed in the silicon substrate 410.

The aforementioned steps shown in FIGS. 25C through 25H and FIGS. 26C through 26H may be substituted with steps shown in FIGS. 25I through 25L and 26I through 26L. Referring to FIGS. 25I and 26I, the insulation coating layer 440 is deposited on the molybdenum layer 433. Then as shown in FIGS. 25J and 26J, after providing a photoresist film, the insulation coating layer 440 is partially etched by a buffer hydrofluoric acid liquid. Further, as shown in FIGS. 25K and 25L and FIGS. 26K and 26L, the layers 431 to 433 are patterned by plasma etching, sputter etching or the like.

Another embodiment of the present invention is described with reference to FIGS. 27A through 27G and FIGS. 28A through 27G. As described previously, in the structure shown in FIGS. 25A through 25L and FIGS. 26A through 26L, the platinum layer 432 is electrically connected to the gas sensitive layer 450 through the layer 431. On the other hand, a platinum layer 532 corresponding to the layer 432 is directly connected to a gas sensitive layer 550 corresponding to the gas sensitive layer 450. It is noted that there is a probability that the presence of the molybdenum layer 431 increases resistance between the molybdenum layer 431 and the gas sensitive layer 450 of tin dioxide. On the other hand, since platinum is hardly oxidized, the above-mentioned increase of the resistance can be avoided.

Referring to FIGS. 27A and 28A, an insulator layer 520 of silicon dioxide is formed on the entire surface of a silicon substrate 510. Then as shown in FIGS. 27B and 28B, a molybdenum layer served as the adhesion reinforcement layer is deposited on the entire surface of the insulator layer 520. Then a portion of the insulator layer corresponding to a pattern of the gas sensitive layer 550, is eliminated by etching in which a rare nitric acid liquid is used. Thereby, a patterned molybdenum layer 531 is formed.

Then, as shown in FIGS. 27C and 28C, a tin dioxide gas sensitive layer is deposited on the entire surface of the structure shown in FIGS. 27B and 28B. Subsequently, only a portion of the gas sensitive layer to be left is coated with a photoresist (not shown), and is subjected to plasma etching. Then the photoresist is removed, so that a patterned gas sensitive layer 550 is formed.

After that, as shown in FIGS. 27D and 28D, a platinum layer 532 and a molybdenum layer 533 are formed in this order, and are then etched so that end portions of the gas sensitive layer 550 are coated by the platinum layer 532. It is noted that the platinum layer 532 is directly connected to the gas sensitive layer 550. The steps which follow the step shown in FIGS. 27D and 28D are the same as those shown in FIGS. 25F through 25H and FIGS. 26F through 26H.

The step shown in FIGS. 27B and 28B may be substituted with a step shown in FIGS. 27H and 28H. That is, after the tin dioxide layer is patterned so as to obtain the patterned gas sensitive layer 550, a molybdenum layer is formed on the entire surface, and is then etched so that a portion thereof on the gas sensitive layer 550 is removed.

Still another embodiment is described with reference to FIGS. 29A through 29K and FIGS. 30A through 30K. This embodiment has a feature that each detection lead is constituted by a single layer 630 of platinum, or in other words, adhesion reinforcement layers are not employed. It is particularly noted that although platinum does not have enough adhesion to silicon dioxide, the platinum layer 630 is put between insulator layers 620 and 651, as shown in FIGS. 29G and 30G.

Referring to FIGS. 29A and 30A, the insulation layer made of silicon dioxide 620 is deposited on the entire surface of a silicon substrate 610. Next as shown in FIGS. 29B and 30B, a tin dioxide layer is deposited and is then patterned so that a gas sensitive layer 650 is formed. Then, as shown in FIGS. 29C and 30C and FIGS. 29D and 30D, a platinum layer 630 is deposited and is then patterned. After that, as shown in FIGS. 29E and 30E and FIGS. 29F and 30F, an insulation coating layer 637 made of silicon dioxide is deposited and is then patterned. Finally, as shown in FIGS. 29G and 30G, a cavity 600 is formed in the silicon substrate 610 by etching.

The steps shown in FIGS. 29C through 29G and FIGS. 30C and 30G may be substituted with steps shown in FIGS. 29H through 29K and FIGS. 30H through 30K. Referring to FIGS. 29H and 30H, after depositing the platinum film 630, an insulation coating layer 540 of silicon dioxide is deposited on the entire surface. Then, as shown in FIGS. 29I and 30I, the insulation coating layer 540 and the platinum layer 630 are partially removed by etching. Subsequently, as shown in FIGS. 29J and 30J, the insulation coating film 540 is partially etched so as to expose portions of the platinum film 630 served as bonding pads. Finally, the cavity 600 is formed in the silicon substrate 610.

Figure 31A:
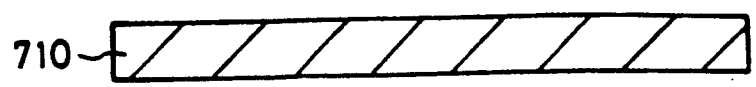
FIGS. 31A through 31D are cross sectional views illustrating a process for producing a still further embodiment of the present invention.
Figure 31B:
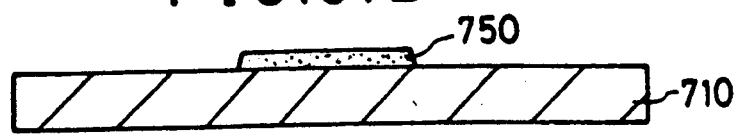

FIGS. 31A through 31D show a still further embodiment of the present invention. FIG. 31A shows a heat-resistant substrate made of ceramics such as alumina and glass. As shown in FIG. 31B, a gas sensitive layer made of tin dioxide is deposited on the entire surface of the substrate 710, and is then patterned so that a patterned gas sensitive layer 750 is formed. Then the gas sensitive layer 750 is sintered. Tin dioxide may be substituted with other metal oxide semiconductor materials such as $Fe_2O_3$, $ZnO$ and $TiO_2$. As described previously, the deposition of tin oxide is done by evaporation, chemical vapor deposition, sputtering or ion plating. Alternatively, it is possible to employ printing which employs a solvent having metal chloride, metal hydroxide, or metal chloride to which a binder such as silica and alumina is added.

Figure 31C:
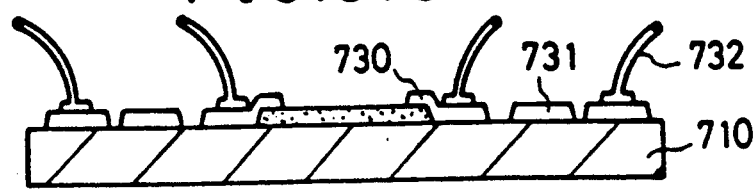
Figure 31D:
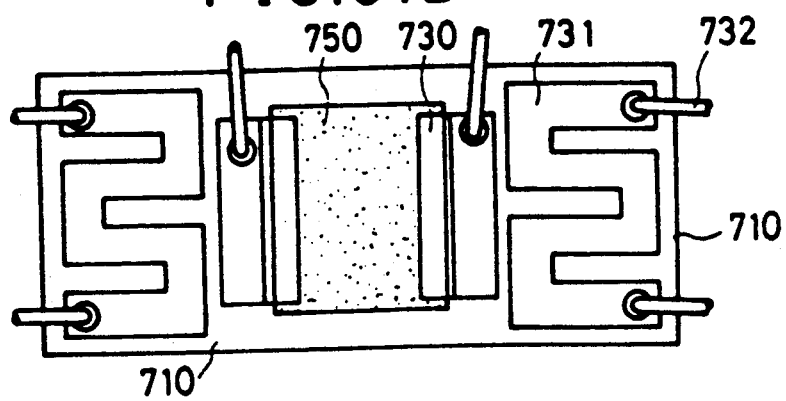

Referring to FIG. 31C, detection leads 730, heater leads 731 and wires 732 for the external connection are formed. It is noted that the detection leads 730 are formed so as to cover opposite end portions of the gas sensitive layer 750.

Figure 32:
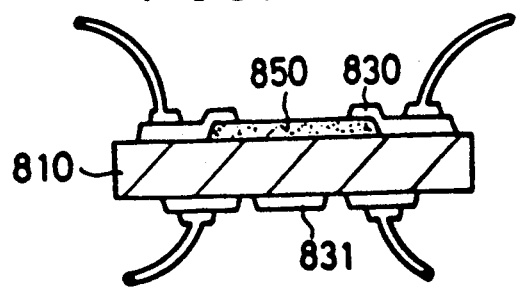
FIG. 32 is a side view of a still further embodiment of the present invention.

FIG. 32 shows a still further embodiment of the present invention. A patterned gas sensitive layer 850 is formed on a surface of a ceramics substrate 810. Detection leads 830 are formed on the same surface so as to cover opposite end portions of the gas sensitive layer 850. A heater lead 831 is formed on an opposite surface of the substrate 831.

An improvement of the aforementioned embodiments is described. As described previously, the insulation layers formed on the substrate, such as the insulation layer 22 shown in FIG. 4 is formed by depositing silicon dioxide by sputtering, evaporation, chemical vapor deposition or ion plating. It is particularly noted that a considerable long time is taken to deposit the insulation layer to a desired thickness, or in other words, the sputtering rate for silicon dioxide is low. For example, 1 to 3 hours are taken to obtain a silicon dioxide film having a thickness of approximately 1 $\mu$m by RF sputtering in which the substrate is set to a temperature of 350°-400° C. Therefore, the mass productivity of sputtering is not high.

In order to improve the productivity of gas detectors, a silicon dioxide film is grown on a silicon substrate by thermal oxidation. This is now described with reference to FIGS. 33A through 33D.

Figure 33A:
FIGS. 33A through 33D are cross sectional views illustrating a process of producing a still further embodiment of the present invention.
Figure 33B:
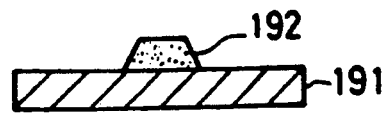
Figure 33C:
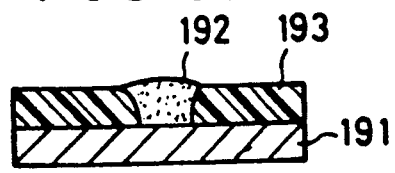
Figure 33D:
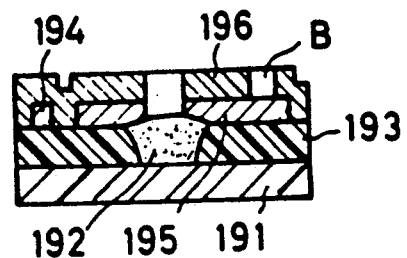

Referring to FIG. 33D, the cross section of an improved gas sensor comprises a silicon substrate 191, a gas sensitive layer 192, a silicon dioxide layer 191, a heat-resistant insulator layer 196, a heater lead 194, and detection leads 195. A character "B" indicates a bonding pad portion. The detection leads 195 are in contact with top portions of the the gas sensitive layer 192. The essential feature of the embodiment of FIG. 33D is that the silicon dioxide layer 193 is formed by thermal oxidation with respect to the silicon substrate 191. On the other hand, the insulator layer 196 is formed by a process other than thermal oxidation, such as sputtering.

Figure 34:
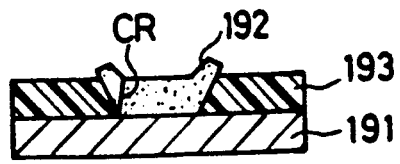
FIG. 34 is a cross sectional view illustrating a problem which may occur in a case where a specific process is not used.

A method for producing the structure of FIG. 33D is described. Referring to FIG. 33A, a gas sensitive layer is deposited to a thickness of 0.05-2 $\mu$m, preferably 0.1-0.2 $\mu$m on the entire surface of the silicon substrate 191 by chemical vapor deposition, evaporation, sputtering or ion plating. Then, the gas sensitive layer is patterned so as to obtain the gas sensitive layer 192. It is preferable to form the gas sensitive layer 192 so that an edge thereof has a taper, as shown in FIG. 33B. The width of the gas sensitive layer 192 is smaller at the top thereof than that at the bottom. This is because if the edge of the gas sensitive layer 192 rises steeply, edges of the gas sensitive layer 192 becomes deformed greatly, as shown in FIG. 34. In detail, there is formed a step may be formed between the gas sensitive layer 192 and the silicon dioxide film 193 which is subsequently formed by the thermal oxidation. The deformation may cause a crack CR in the gas sensitive layer 192, as shown in FIG. 34.

Subsequent to step of FIG. 33B, the silicon substrate 191 is subjected to thermal oxidation. It is preferable to perform the thermal oxidation at a temperature as low as possible in order to reduce the deformation of the gas sensitive layer 192. A temperature range of 600°-1000° C., preferably 700-900° C. can be selected. The silicon dioxide layer 193 is grown so as to have a thickness capable of providing enough insulation. From this viewpoint, a thickness of 0.05-0.3 $\mu$m, preferably 0.1-0.2 $\mu$m is selected. By this step, the insulator layer 193 is formed as shown in FIG. 33C.

It is noted that when the silicon substrate 191 is subjected to thermal oxidation, the silicon dioxide film 193 is formed so that it goes under the gas sensitive layer 192. Thereby, it is possible to reduce the step formed on the surface of the gas sensitive layer 192, or in other words, make the surface of the gas sensitive layer 192 flat. As a result, it is possible to form layers on the surface of the gas sensitive layer 192 with ease.

Then, the heater lead 194 and the detection leads 195 are formed The heater leads 194 and the detection leads 195 may be made of materials described previously. Thereafter, the heat-resistant insulator layer 196 is deposited to a thickness of 0.2-2.0 $\mu$m, preferably 0.1-0.8 $\mu$m by sputtering, chemical vapor deposition, ion plating or evaporation. The heat-resistant insulator layer 196 may be made of materials described previously. Finally, the insulator layer 196 are partially etched so as to expose the bonding pad portion B of the detection lead 195.

The formation of the insulator layer by thermal oxidation for the silicon substrate is applicable to not only the above-mentioned embodiments but also embodiments described hereinafter.

A description is given of materials used for detection leads. As described previously, various materials are used to form the gas detection leads which extend from the gas sensitive layer. The present inventors found in the experiment that platinum is especially suitable for forming detection leads.

Figure 35:
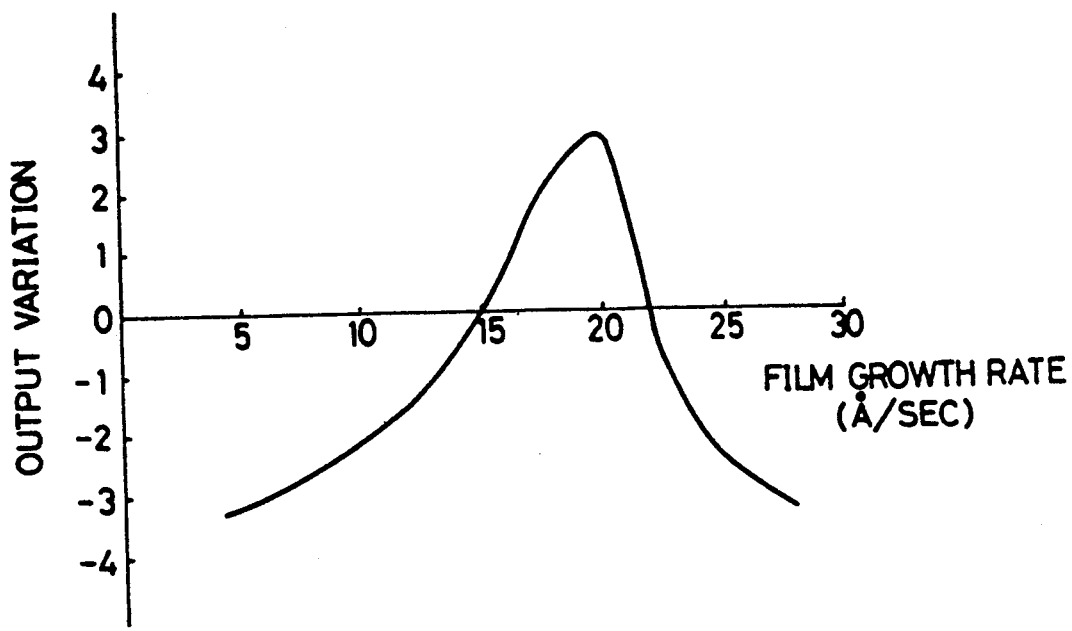
FIG. 35 is a graph showing the relationship between the output voltage of a gas detector and the film growth rate.

The inventors noted a variation with time in properties of metal oxide semiconductor materials used for forming the gas sensitive layer. The inventors investigated a variation with time in properties of a tin dioxide ($SnO_2$) film formed by a thin-film evaporation apparatus disclosed in Japanese Laid-Open Patent Application No. 59-89763. The result of the investigation is illustrated in FIG. 35. FIG. 35 shows the relationship between a quantity of a variation in an output of the tin dioxide film and a film growth rate (Å/sec), which was observed with the pressure of oxygen ($P_{O2}$) set equal to 0.5 Pa (pascal). The quantity of a variation in an output of the tin dioxide film was obtained as follows. A tin dioxide film was placed on a ceramics heater which was kept at a temperature of 500° C. In the experiment, a plurality of tin dioxide films grown at different film growth rate were prepared. Then when the tin dioxide film went up to 500° C., the application of a voltage to the tin dioxide film was started. Then the output voltage of the tin dioxide film was measured for ten hours. Then the quantity of a variation in the output voltage during the above term was divided by the output voltage immediately after the application of the voltage. A value thus obtained is the quantity of a variation in an output of the tin dioxide film. In FIG. 35, the value is represented as a relative value. The output voltage of the tin dioxide film was measured as follows. Two probes were spaced at a predetermined distance and directly made contact with the tin dioxide film. The probes were formed by plating a copper alloy with gold. A current was made flow across the two probes, and a voltage across the probes was measured Since resistance of a tin dioxide film reduces greatly in an initial stage of the annealing process, each of the tin dioxide films prepared were annealed in an air at 500° C. for three hours prior to the measurement.

It can be seen from FIG. 35 that when $P_{O2}=0.5$ Pa, a tin dioxide film grown at a film growth rate of 15 Å/sec or 22 Å/sec has less variation in output voltage. Additionally, it was found that this property hardly changes for a film thickness of 0.05-2 μm.

In order to select materials suitable for forming detection leads, a plurality of gas detectors each having the structure of FIG. 31C were prepared in which various materials were used to form the detection leads 730. The gas sensitive layer 730 was constituted by a tin dioxide film obtained under conditions that $P_{O2}=0.5$ Pa, and the film growth rate is 15 Å/sec. The prepared samples were kept at a temperature of 500° C.

Figure 36:
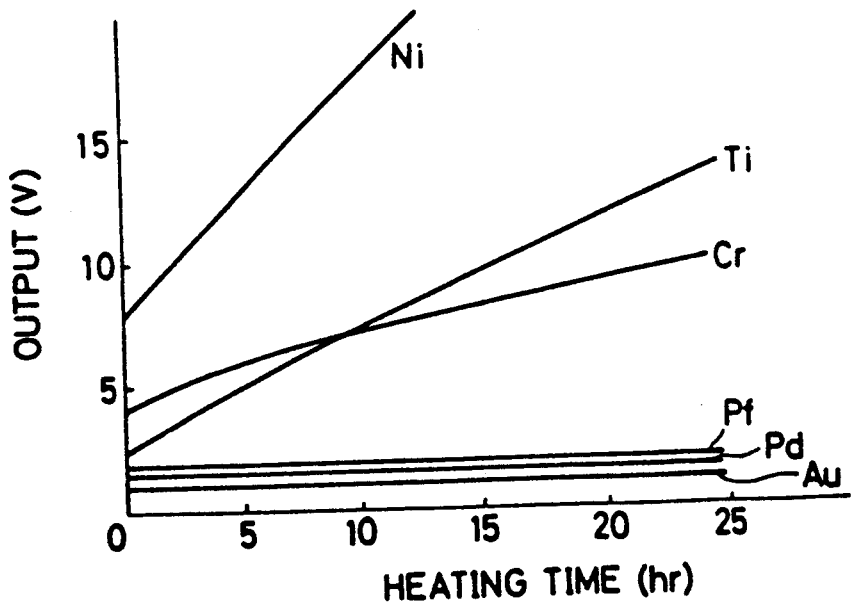
FIG. 36 is a graph showing the relationship between the output voltage of a gas detector and heating time.

FIG. 36 shows experimental results. The horizontal axis of FIG. 36 represents a time during which the voltage was applied to the heater leads 731. The vertical axis of FIG. 36 represents the output voltage of the gas sensitive layer 750, or detector output voltage. Variations in the outputs of the prepared gas detectors as a function of time differ in different gas detectors. The difference in variations mainly results from the event in which the detection leads 730 themselves are oxidized, and the event that the detection leads 730 come off the gas sensitive layer 750. It can be seen from FIG. 36 that platinum, palladium and gold are suitable for materials used for forming detection leads. It is noted that gold may have some problem in view of adhesion to the substrate. It is also noted, and that palladium may have some problem in which oxygen atoms are diffused into the palladium film due to the thermal oxidation process and reach an interface with the gas sensitive layer 750 of tin dioxide. Particularly, properties of detection leads of palladium may be considerably degraded under hard conditions. On the other hand, it was found that platinum does not exhibit the above-mentioned problems, and is an optimum material for detection leads.

Figure 37:
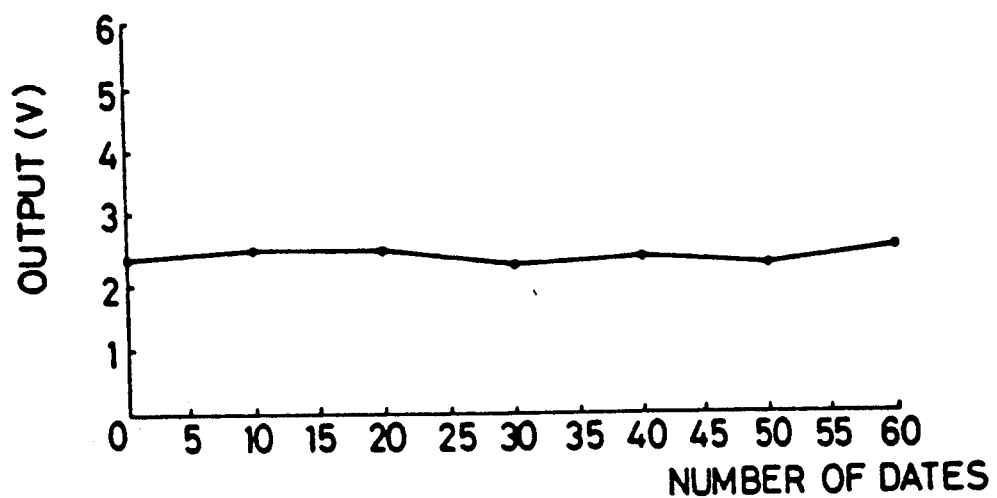
FIG. 37 is a graph showing the time variation in the output voltage of the gas detector.

FIG. 37 shows the output voltage characteristic of a gas detector having the structure of FIG. 31C in which the detection leads 730 were made of platinum, and the gas sensitive layer 750 was grown at a pressure of $P_{O2}=0.5$ Pa at a film growth rate of 15 Å/sec. In this experiment, the gas detector placed in an air was heated to 500° C. for three hours before the measurement, and was kept at a temperature of 450° C. during the measurement. FIG. 37 reveals that platinum are especially suitable for a material for detection leads.

The inventors has found that although tin dioxide is one of the optimum materials as a gas sensitive material, detection leads made of platinum are also suitably used in combination with a gas sensitive layer comprising an oxide of titanium, indium, tungsten, nickel, zinc, iron or cadmium. In this case, it is preferable to form the above gas sensitive layer to a thickness of 0.05-2 μm.

In the embodiments described above, a pair of detection leads such as 23a and 23b shown in FIG. 3 are made of the same material. However, the inventors found that an output voltage stable over a long term is obtainable by forming one of a pair of detection leads with a material different from that of the other of the detection leads.

The inventors found the above in the experiment in which gas detectors having three different structures shown in FIGS. 38A, 38B, 38C, and 39. Each of the gas detectors shown in FIGS. 38A and 38B, and FIG. 39 is made up of a heat-resistant substrate 168, a heater film 169 to which bonding wires 161 and 162 are connected, an insulator film 167 to which bonding wires 171 and 172 are connected, detection leads 163 and 164 to which bonding wires 171 and 172 are connected, and a gas sensitive layer 165. The gas detector shown in FIG. 38C is made up of an insulating heat-resistant substrate 174, a gas sensitive layer 52, detection leads (electrodes) 175 and 176, and lead pins 173. The detection leads 175 and 176 also function as heater coils.

In the experiment, the detection leads 163, 164, 175 and 176 were made of various materials. The gas sensitive layers 165 and 177 were made of tin dioxide. Then the output voltage of the gas sensitive layers 165 and 177 as a function of time were measured.

Figure 40:
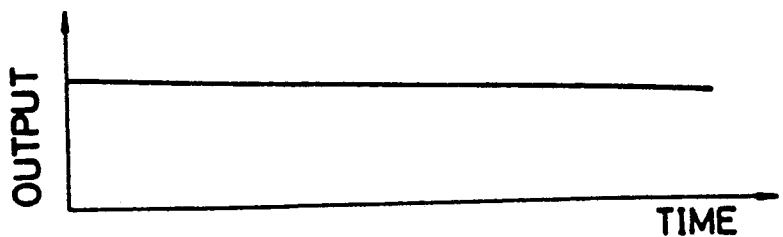
FIGS. 40 through 42 are graphs showing the relationship between the output voltage of the gas detector and time.

FIG. 40 shows a time-varying detector output voltage for each of the three type gas detectors. In this case, the detection leads 163, 164, 175 and 176 were made of platinum. Each of the gas detectors was placed in a clean air in which there is no gas, and was heated to 300°-400° C. It can be seen from FIG. 40 that the detector output voltage decreases gradually as time goes on.

Figure 41:
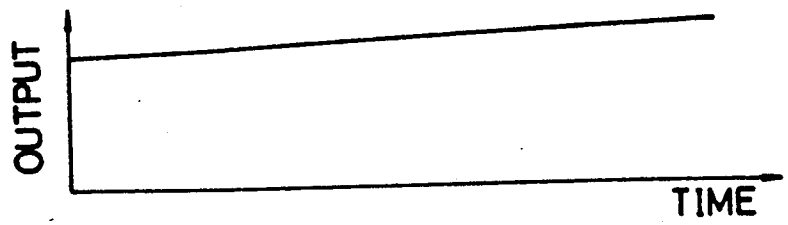

FIG. 41 shows a time-varying detector output voltage for each of the three types. In this case the detection leads 163, 164, 175 and 176 were made of tin. Other conditions are the same as in the case of FIG. 40. It can be seen from FIG. 41 that the detector output voltage increases gradually as the time goes on.

Figure 42:
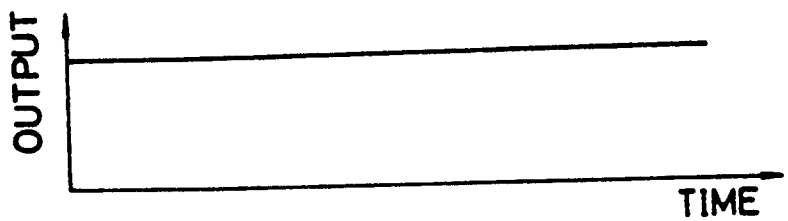

An embodiment of the present invention described below is based on the above-mentioned experiment. That is, this embodiment intends to obtain the detector output voltage stable over a longer time. That is, in a case where the detection lead 163 (175) is made of platinum, and the detection lead 164 (176) is made of chromium, a variation in the detector output voltage as a function of time can be compensated, whereby the stabilized sensor output is obtainable over an extremely long term, as shown in FIG. 42.

Gold and palladium have the characteristic as shown in FIG. 40 as in the case of platinum. That is, the detector output voltage decreases as time goes on. On the other hand, titanium and nickel have the characteristic as shown in FIG. 41 as in the case of chromium. Further, a multilayer structure of the detection lead which includes at least one layer containing chromium, titanium or nickel, has the characteristic as shown in FIG. 41. For example, platinum/chromiun, gold/platinum/chromiun, or platinum/titanium exhibits the characteristic as shown in FIG. 42.

A combination of platinum and chromium is a particularly preferable selection. Although the above-mentioned embodiment uses the tin dioxide gas sensitive layer, the use of different materials for forming a pair of detection leads is not limited to the tin dioxide gas sensitive layer, but is applicable to the gas sensitive layer made of an oxide of titanium, indium, tungsten, nickel, zinc or iron.

A description is given of a method for producing the gas detector of FIGS. 38A and 38B with reference to FIGS. 43A through 43E.

Figure 43A:
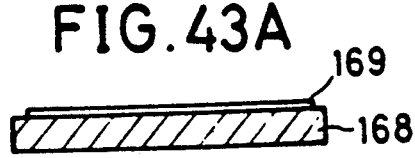
FIGS. 43A through 43E are cross sectional views illustrating a process of the structure shown in FIGS. 38A and 38B.
Figure 43B:
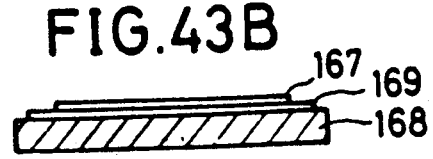
Figure 43C:
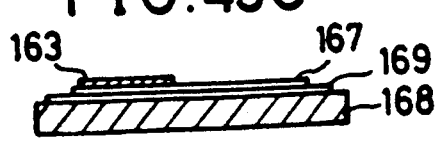
Figure 43D:
Figure 43E:
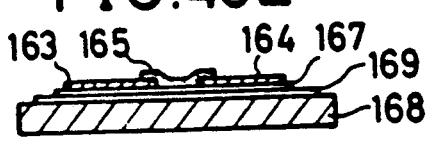

Referring to FIG. 43A, the heater film 169 is formed on the heat-resistant substrate 168. Then, as shown in FIG. 43B, the insulator film 167 is formed on the substrate 168 so as to be surrounded by the heater film 169. Thereafter, as shown in FIGS. 43C and 43D, by using the photolithography technique, the detection leads 163 and 164 are formed on the insulator film 167. Then, the gas sensitive layer 165 is formed so as to partially overlie the detection leads 163 and 164. Finally, the lead wires 161, 162, 171 and 172 are attached as shown in FIGS. 37A and 37B.

Figure 44A:
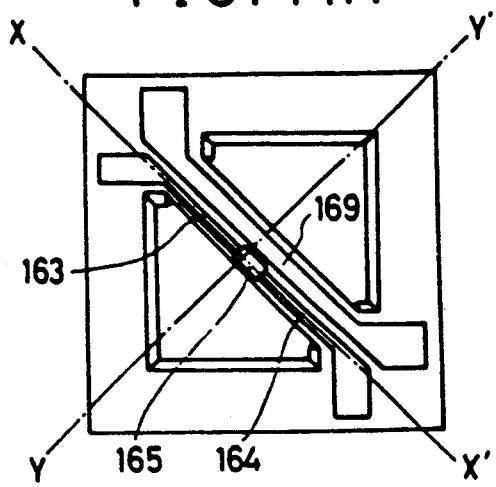
FIGS. 44A through 44C are views of a gas detector having the feature found by the experimental results illustrated in FIGS. 40 through 42.
Figure 44B:
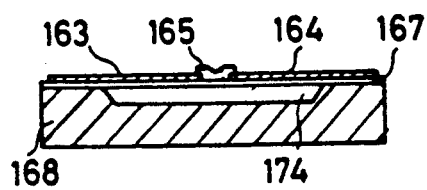
Figure 44C:
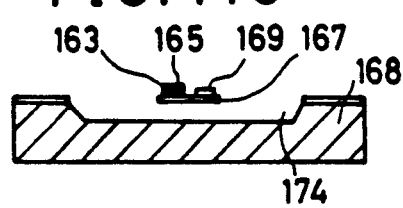
Figure 45A:
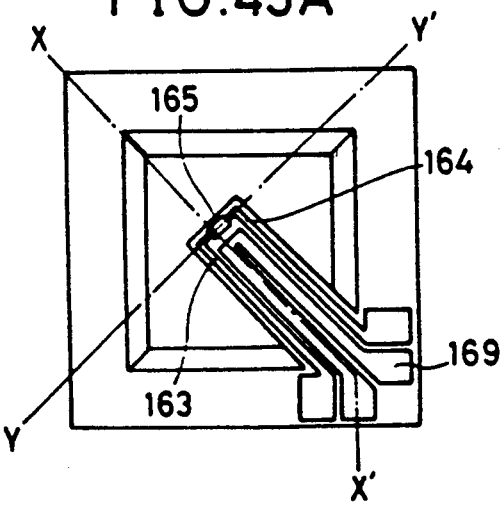
FIGS. 45A through 45C are views of a gas detector having the feature found by the experimental results illustrated in FIGS. 40 through 42.
Figure 45B:
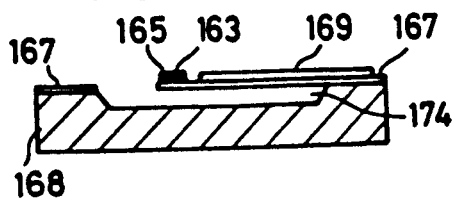
Figure 45C:
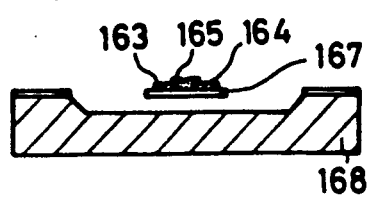

FIGS. 44A through 44C show a gas detector of the micro-heater structure type in which the detection lead 163 is made of a material different from a material of the detection lead 164. FIGS. 44B and 44C are cross sectional views taken along lines X—X' and Y—Y' shown in FIG. 44A. FIGS. 45A through 45C show a gas detector of the micro-heater structure type in which the detection lead 163 is made of a material different from a material for the gas detection lead 164. FIGS. 45B and 45C are cross sectional views taken along lines X—X' and Y—Y' shown in FIG. 45A.

The arrangement in which the detection lead 163 or 175 is made of a material different from that of the detection lead 164 or 176, is applicable to not only the aforementioned embodiments but also embodiments described hereafter.

In the above-mentioned embodiments, gas sensitive layers such as 25 (FIG. 4) is formed on insulator layers such as 22 (FIG. 4). In the embodiment of FIG. 4, the upper surface of the gas sensitive layer 25 is exposed to gas, and the bottom surface thereof is in contact with the insulator layer 22. This holds true for the other embodiments described previously.

An embodiment described below has an essential feature that the bottom surface of a gas sensitive layer is exposed to gas. Such an embodiment is described with reference to FIGS. 46, 47 and 48.

Referring to these figures, an insulator layer 236 is laid across a cavity 235 between corner portions of a silicon substrate 231 having a cavity 235. A gas sensitive layer 232 is formed so as to be buried in the insulator layer 236. Detection leads 233a and 233b are formed on the insulator layer 236. End portions of the detection leads 233a and 233b overlie the gas sensitive layer 232. A heater lead 233c is also formed on the insulator layer 236. An insulation coating layer 234 is provided so as to cover the detection leads 233a and 233b, and the heater lead 233c. The bottom surface of the gas sensitive layer 232 is served as a gas detection surface, or in other words, exposed to gas.

Figure 46:
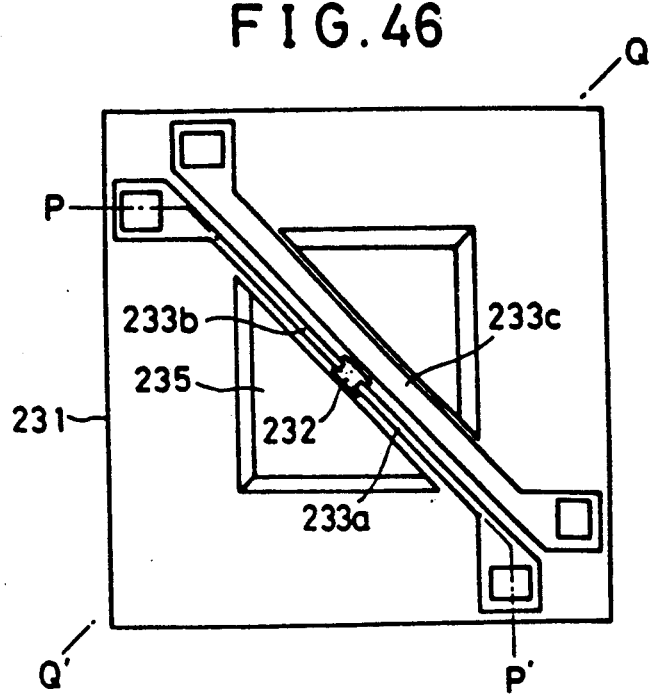
FIG. 46 is plan view of an embodiment of the present invention in which a gas sensitive layer is formed so as to be buried in an insulator layer.
Figure 47:
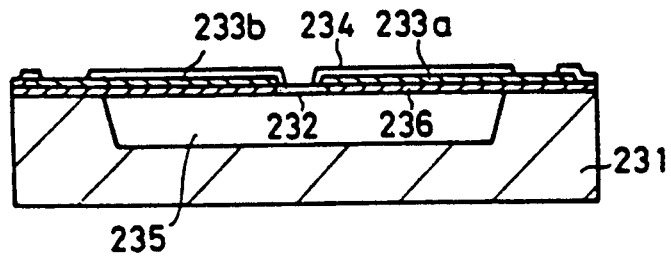
FIG. 47 is a cross sectional view taken along a line P—P' shown in FIG. 46.
Figure 48:
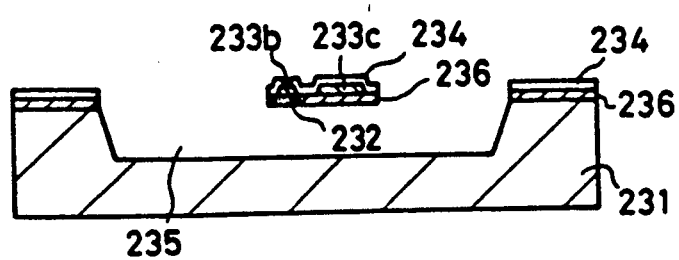
FIG. 48 is a cross sectional view taken along a line Q—Q' shown in FIG. 46.

A description is given of a process for producing the gas detector shown in FIGS. 46 through 48 by referring to FIGS. 49A through 49L, and FIGS. 50A through 50L. Although each of the detection leads 233a and 233b, and the heater lead 233c shown in FIGS. 46 through 48 is constituted by a single layer, the gas detector produced by the process described below is with respect to a case where each of the detection leads 233a and 233b, and the heater lead 233c is sandwiched between adhesion reinforcement layers.

Referring to FIGS. 49A and 50A, the gas sensitive layer 232 of silicon dioxide is formed on the silicon substrate 231 to a thickness of 0.05–2 $\mu$m by evaporation, sputtering ion plating, or chemical vapor deposition. Next, the gas sensitive layer is patterned by etching. Then, as shown in FIGS. 49B and 50B, the insulator layer 236 is formed on the silicon substrate 231 to a thickness of 0.1–2 $\mu$m. The insulator layer 236 is made of $SiO_2$, $Si_3N_4$, $Al_2O_3$, $MgF_2$, $TaO_5$ or the like. Subsequently, an adhesion reinforcement layer 241 of Cr, Mo, Ni, Ti or the like is formed to a thickness of 0.05–0.1 $\mu$m. Then the adhesion reinforcement layer 241 and the insulator layer 236 are partially removed so that the gas sensitive layer 232 is exposed. In a case where the adhesion reinforcement layer 241 is made of Mo, it is etched by rare nitric acid, and in a case where the insulator layer 232 is made of $SiO_2$, it is etched by buffer hydrofluoric acid.

In place of steps of FIGS. 49A, 49B, 50A and 50B, steps shown in FIGS. 49H, 49I, 50H and 50I may be used. Referring to FIGS. 49H and 50H, the insulator layer 236 and the adhesion reinforcement layer 241 are formed in this order on the silicon substrate 231. Then as shown in FIGS. 49I and 50I, these layers 236 and 241 are subjected to etching in which a position at which the gas sensitive layer 232 is to be formed. Then, as shown in FIGS. 49I and 50I, the gas sensitive layer 232 is formed on the entire surface of the silicon substrate 231, and is then patterned by photoetching. The level at the top of the gas sensitive layer 232 is equal to that at the top of the insulator layer 236. Thereby, the structure shown in FIGS. 49C and 50C are obtained.

Referring to FIGS. 49D and 50D, a layer 242 is grown to a thickness of 0.1–2 $\mu$m. Subsequently, a layer 243 is grown to a thickness of 0.05–0.1 $\mu$m. The layers 242 and 243 are used together with the layer 241 to form the detection leads 233a and 233b, and the heater lead 233c. The layer 243 functions as the adhesion reinforcement layer as in the case of the layer 241. The layer 242 is made of a conductive material such as Pt, Rh, Ir, Pd, Ni, Cr, Mo, W or Ta, or an alloy thereof such as PtIr, NiCr, SiC, TaN or kanthal. The layer 243 is made of a conductive material identical to that for the layer 241.

Referring to FIGS. 49E and 50E, the layers 241 to 243 are patterned so as to form the detection leads 233a and 233b, and the heater lead 233c. Then as shown in FIGS. 49F and 50F, the insulation coating layer 234 of silicon dioxide is grown to a thickness of 0.1–0.2 $\mu$m, and is then patterned by photoetching so as to form openings for exposing bonding pads, an etching window for a cavity 235 (FIGS. 49G and 50G), an opening above the gas sensitive layer 232. Finally, as shown in FIGS. 49G and 50G, the silicon substrate 231 is etched by using NaOH so that the cavity 235 is formed therein.

In place of steps shown in FIGS. 49D through 49G and FIGS. 50D through 50G, steps shown in FIGS. 49J through 49L and FIGS. 50J through 50L may be employed Referring to FIGS. 49J and 50J, the SiO$_2$ insulation coating layer 234 (0.1–2 μm thick) is grown on the adhesion reinforcement layer 243, and is then patterned by photoetching or plasma etching so as to form the detection leads 233a and 233b, and the heater lead 233c. Then as shown in FIGS. 49K and 50K, the layers 241, 242, 243 and 234 are patterned by photoetching so as to obtain form openings for use in bonding pads, the etching window for the cavity 235 (FIGS. 49G and 50G), the opening above the gas sensitive layer 232. Finally, as shown in FIGS. 49L and 50L, the silicon substrate 231 is etched so that the cavity 235 is formed therein.

Figure 51:
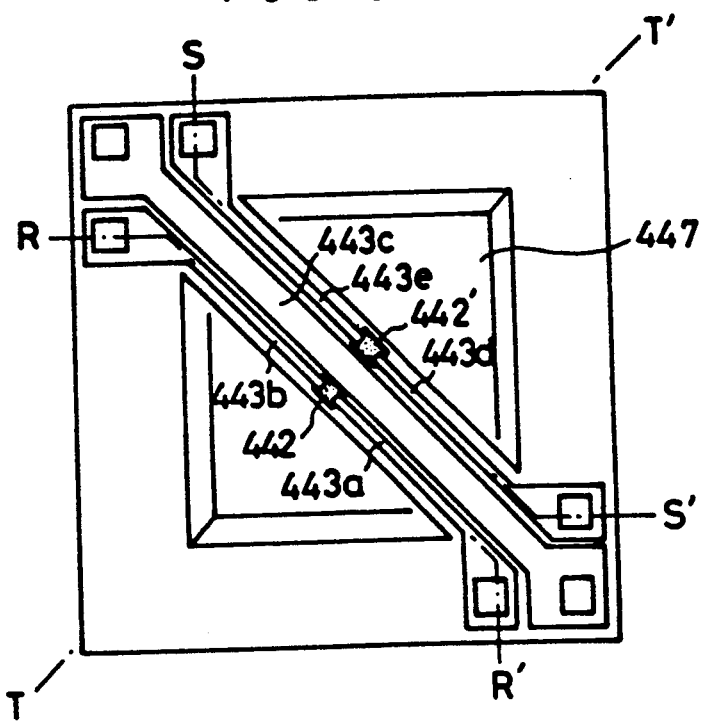
FIG. 51 is a plan view of another embodiment of the present invention in which the gas sensitive layer is buried in the insulator layer.
Figure 52:
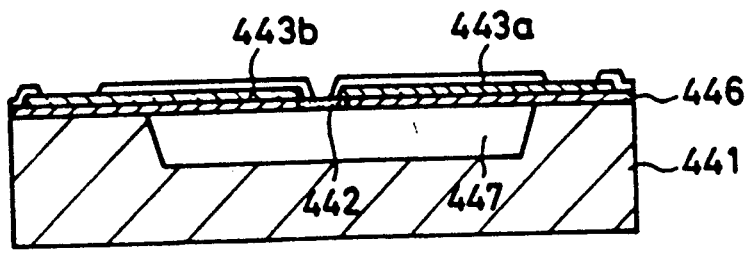
FIG. 52 is a cross sectional view taken along a line R—R' shown in FIG. 51.
Figure 53:
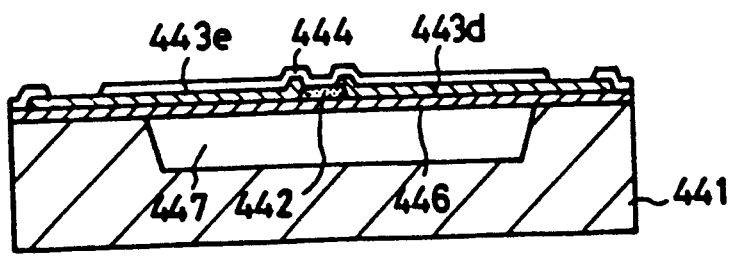
FIG. 53 is a cross sectional view taken along a line S—S' shown in FIG. 51.
Figure 54:
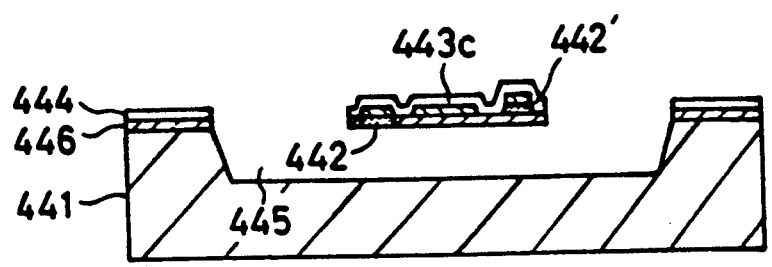
FIG. 54 is a cross sectional view taken along alone T—T' shown in FIG. 51.

A description is given of an embodiment in which an insulator layer extends over two portions with reference to FIGS. 51 through 53. Referring to these figures, an insulator layer 446 extends over two corner portions of a silicon substrate 441. A gas sensitive layer 442 is formed so as to be buried in the insulator layer 446. A temperature sensitive layer 442' is formed on the insulator layer 446. On the insulator layer 446, there are formed detection leads 443a and 443b, leads 443d and 443e, and a heater lead 443c. As shown in FIG. 52, the detection leads 443a and 443b partially overlie the detection leads 442. As shown in FIG. 53, the leads 443c and 443d overlie end portions of the temperature sensitive layer 442'. A cavity 447 is formed in the silicon substrate 441. The bottom surface of the gas sensitive layer 442 is exposed to the cavity 447.

A process for producing the gas detector shown in FIGS. 51 through 53 is described with reference to FIGS. 55A through 55H, FIGS. 56A through 56H, and FIGS. 57A through 57H, which are with respect to the lines R—R', S—S' and T—T' of FIG. 51, respectively.

Referring to FIGS. 55A, 56A and 57A, the insulator layer 446 of silicon dioxide is formed on the silicon substrate 441, and is then patterned by photoetching so as to form an opening at a position at which the gas sensitive layer 442 is to be formed, as shown in FIGS. 55B, 56B and 57B. Next, as shown in FIGS. 55C, 56C and 57C, the gas sensitive layer of tin dioxide is formed on the entire surface, and is then patterned by photoetching or plasma etching so as to form the gas sensitive layer 442 and the temperature sensitive layer 442'.

Then, as shown in FIGS. 55D, 56D, and 57D, a conductive layer of platinum and an insulator layer 440 of silicon dioxide are formed. Subsequently, the insulator layer 440 is partially etched, as shown in FIGS. 55D, 56D and 57D. Then, as shown in FIGS. 55E, 56E and 57E, the platinum layer is etched by plasma etching in which the patterned insulator layer 440 is used as a mask. Then, the insulator layer 440 is removed in its entirety, as shown in FIGS. 55F, 56F and 57F. Alternatively, it is possible to obtain the structure of FIGS. 55F, 56F and 57F without forming the insulator layer 440 in the step of FIGS. 55D, 56D and 57D.

Then, as shown in FIGS. 55G, 56G and 57G, the insulation coating layer 444 of silicon dioxide is formed on the entire surface of the silicon substrate 441, and is then etched so as to obtain opening for bonding pads, an exposure above the gas sensitive layer 442 and a window for forming the cavity 447 (FIGS. 51 through 53). Then the silicon substrate 441 is etched so as to form the cavity 447.

Figure 58:
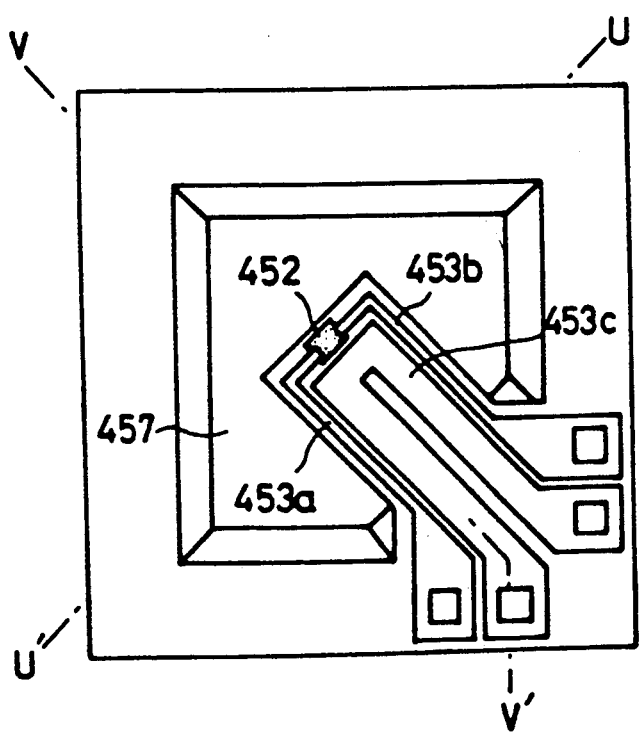
FIG. 58 is a plan view of still another embodiment of the present invention in which the gas sensitive layer is formed so as to be buried in the insulator layer.
Figure 59A:
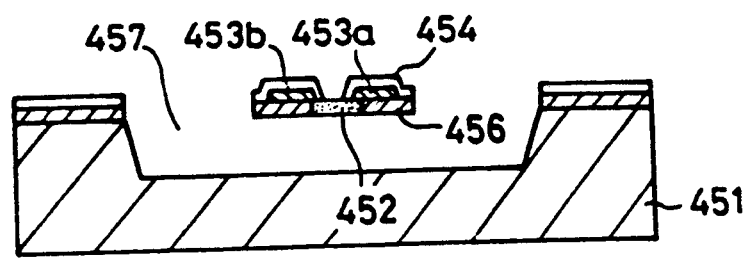
FIG. 59A is a cross sectional view taken along a line U—U' shown in FIG. 58.
Figure 59B:
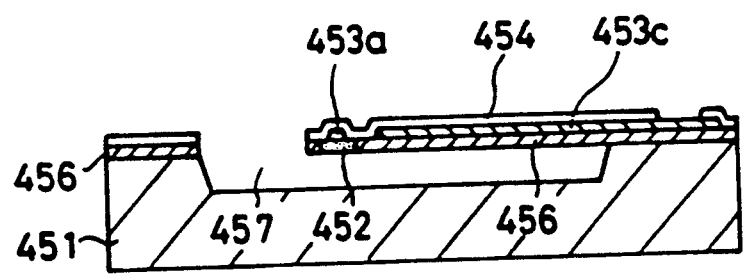
FIG. 59B is a cross sectional view taken along a line V—V' shown in FIG. 58.

Still another embodiment of the present invention is described with reference to FIGS. 58, 59A and 59B. In this embodiment, an insulator layer 456 is supported to a corner portion of a silicon substrate 451. A gas sensitive layer 452 is formed so as to be buried in the insulator layer 456. On the insulator layer 456, there are formed detection leads 453a and 453b, and a heater lead 453c. The detection leads 453a and 453b partially overlie the gas sensitive layer 452. The detection leads 453a and 453b and the heater lead 453c are covered with an insulation coating layer 454. The upper surface of the gas sensitive layer 452 is exposed, and the bottom surface thereof is exposed to a cavity 457 formed in the silicon substrate 451.

Figure 60:
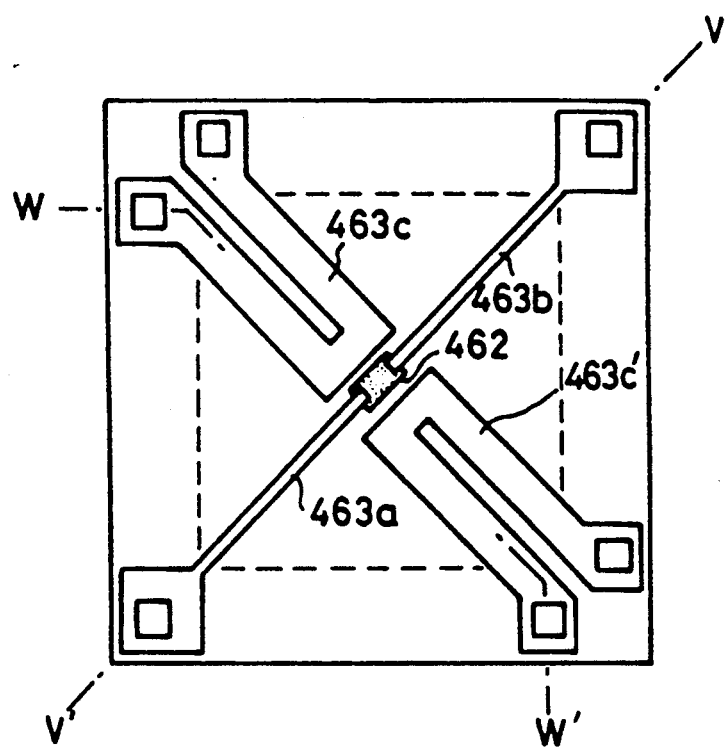
FIG. 60 is a plan view of a further embodiment of the present invention in which the gas sensitive layer is formed so as to be buried in the insulator layer.
Figure 61A:
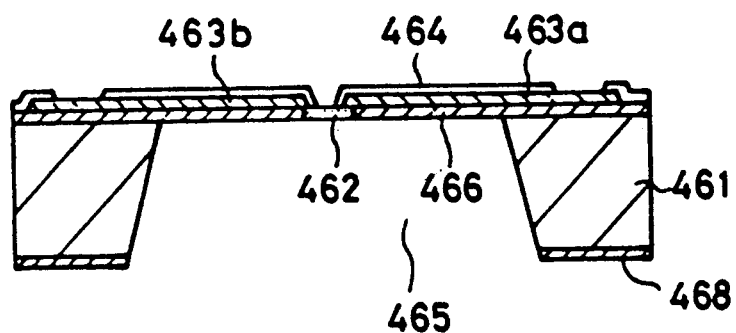
FIG. 61A is a cross sectional view taken along a line V—V' shown in FIG. 60.
Figure 61B:
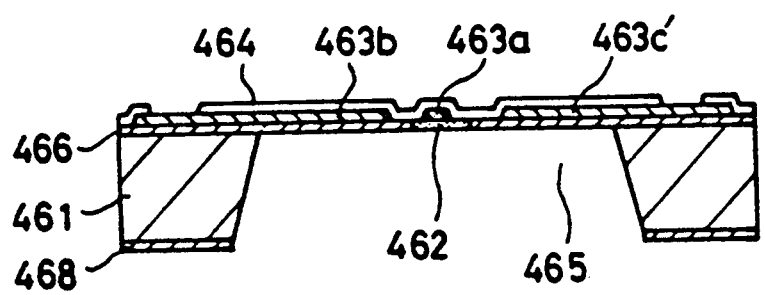
FIG. 61B is a cross sectional view taken along a line W—W' shown in FIG. 60.

A further embodiment of the present invention is described with reference to FIG. 60, 61A and 61B. This embodiment is of a diaphragm type. A cavity 465 is formed in a silicon substrate 461. An insulator layer 466 extends over two corner portions of the silicon substrate 461. A gas sensitive layer 462 is formed so as to be buried in the insulator layer 466. On the insulator layer 466, there are formed detection leads 463a and 463b, and heater leads 463c and 463c'. The detection leads 463a and 463 are formed so as to cross the heater leads 463c and 463c'. End portions of the detection leads 463a and 463b overlie the gas sensitive layer 466. An insulation coating layer 464 is provided so as to cover the detection leads and the heater leads 463c and 463c'. A top surface of the gas sensitive layer 462 is exposed. An etching mask 468 is formed on the bottom surface of the silicon substrate 461. The silicon substrate 461 is etched by using the etching mask 468.

Figure 62:
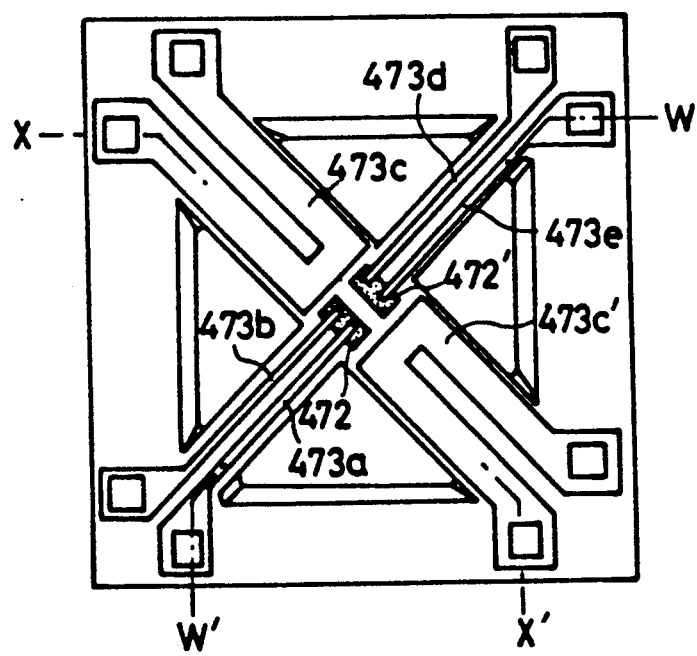
FIG. 62 is a plan view of a still further embodiment of the present invention in which the gas sensitive layer is formed so as to be buried in the insulator layer.
Figure 63:
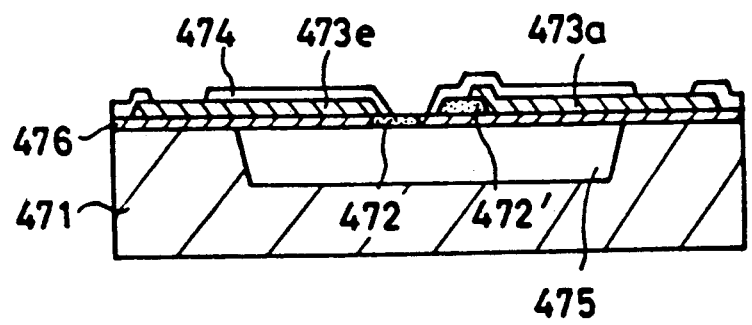
FIG. 63 is a cross sectional view taken along a line W—W' shown in FIG. 62.
Figure 64:
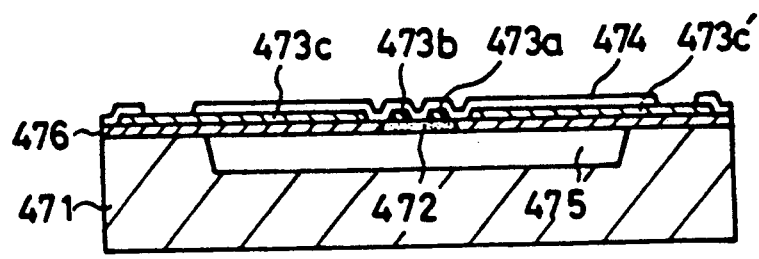
FIG. 64 is a cross sectional view taken along a line X—X' shown in FIG. 62.

A still further embodiment of the present invention is described with reference to FIGS. 62, 63 and 64. A silicon substrate 475 has a cavity 475. An insulator layer 476 is of a cross shape. A gas sensitive layer 472 is formed so as to be buried in the insulator layer 476. Detection leads 473a and 473b are formed on the insulator layer 476. The detection leads 473a and 473b arranged in parallel to each other partially overlie the gas sensitive layer 472. A temperature sensitive layer 472' is formed on the insulator layer 476. Leads 473c and 473c' partially overlie and extend from the temperature sensitive layer 472'. Heater leads 473c and 473d are arranged on the insulator layer 476 so as to form a cross with the leads 473a, 473b, 473d and 473e. An insulation coating layer 474 is formed so as to cover the entire surface except for the surface of the gas sensitive layer 472 and so on. The temperature sensitive layer 472' is totally covered with the insulation coating layer 474.

Figure 65:
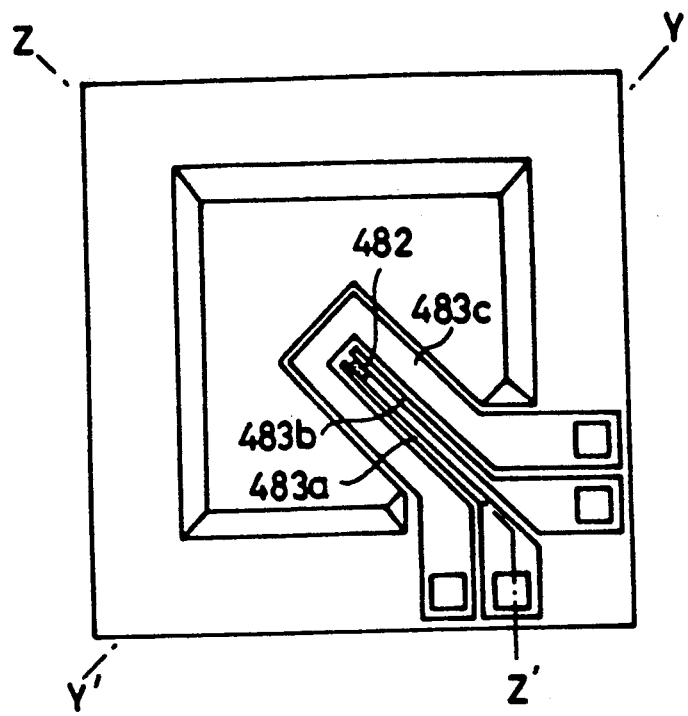
FIG. 65 is a plan view of a still further embodiment of the present invention in which the gas sensitive layer is formed so as to be buried in the insulator layer.
Figure 66:
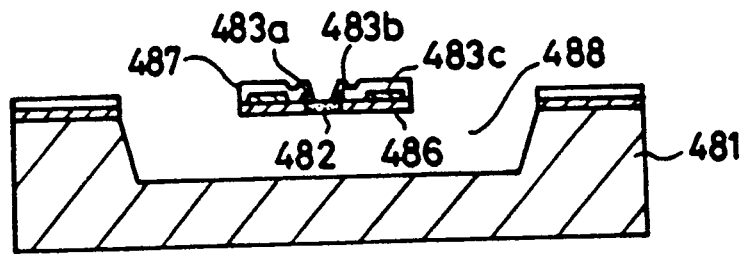
FIG. 66 is a cross sectional view taken along a line Y—Y' shown in FIG. 65.
Figure 67:
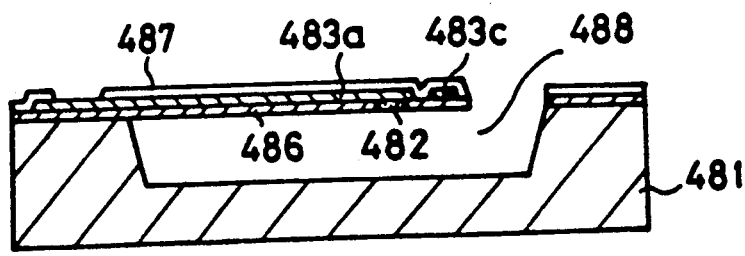
FIG. 67 is a cross sectional view taken along a line Z—Z' shown in FIG. 65.

A still further embodiment of the present invention is described with reference to FIGS. 65, 66 and 67. This embodiment is a variation shown in FIGS. 58, 59A and 59B. As shown, a heater lead 483c is arranged outside detection leads 483a and 483b. The detection leads 483a and 483b partially overlie a gas sensitive layer 482, which is formed so as to be buried in an insulator layer 486 supported on a corner portion of a silicon substrate 481. An insulation coating layer 487 is formed to cover the entire surface of the silicon substrate 481 except for an upper surface of the detection lead 482. A cavity 488 is formed in the silicon substrate 481.

Figure 68:
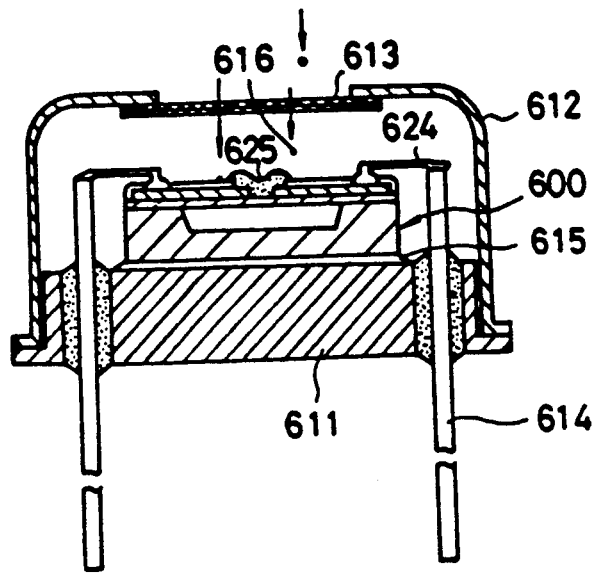
FIGS. 68 through 70 are views which illustrate conventional hermetic seal.
Figure 69:
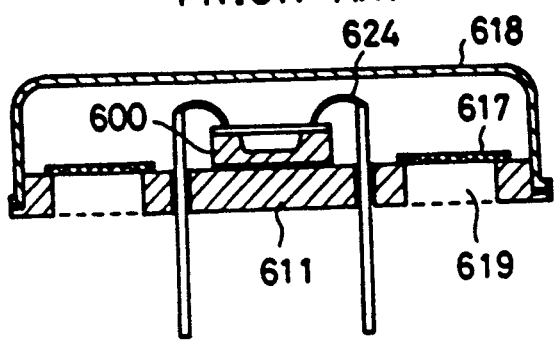
Figure 70:
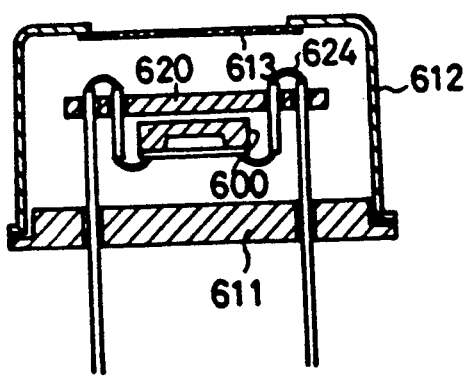

It is preferable that in practical use, the above-mentioned embodiments are hermetically sealed. Conventionally, gas detectors are hermetically sealed as shown in FIGS. 68 through 70. Referring to FIG. 68, a gas detector 600 is mounted on and fixed to a base 611 by a bonding material layer 615. Detection leads connected to a gas sensitive layer 625 are connected to lead terminal pins 614 through wires 624. Since the surface of the gas sensitive layer 625 is arranged so as to be exposed, the gas sensitive layer 625 is contaminated by dust, which degrades the sensitivity of the gas detection. In order to avoid this problem, a cap for use in an electrically programmable random access memory device is utilized. Such a cap is indicated by a reference numeral 612 in FIG. 68. The cap 612 has a cutout portion, which is covered with a stainless mesh. However, even with this structure, it is impossible to avoid dust.

In order to overcome the above-mentioned problem, a structure shown in FIG. 69 has been proposed. The base 611 has through holes 619, which are covered with stainless meshes 617. A cap having no cutout is hermetically fixed to the base 611. A structure shown in FIG. 70 has also been proposed. The gas detector is turned upside down.

However, the structures shown in FIGS. 69 through 70 have disadvantages described below. The gas detectors have a complicated structure, and an increased number of parts are needed. Therefore, the production process is complex, and therefore the gas detectors are expensive.

Figure 71:
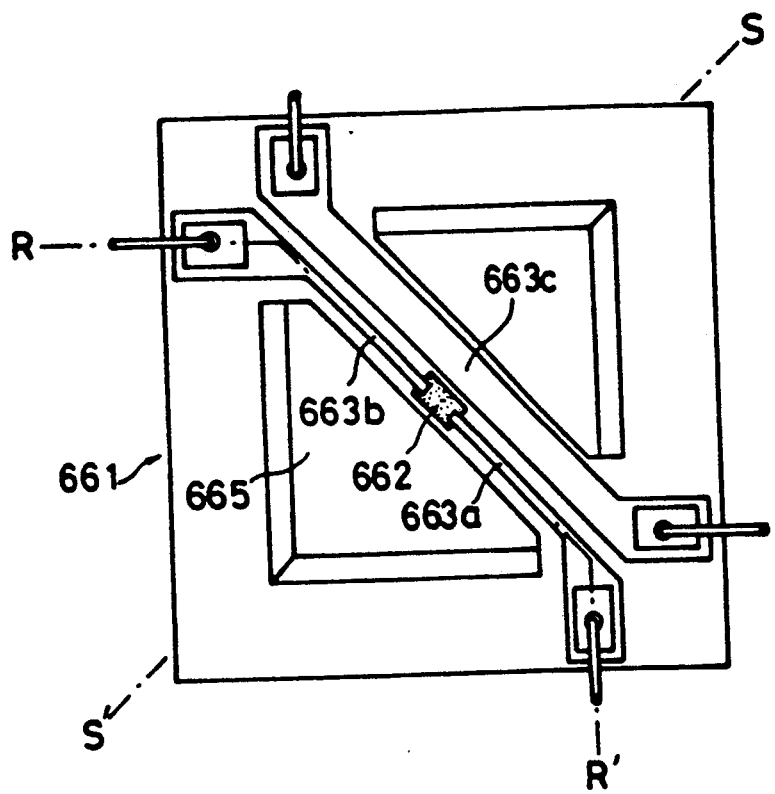
FIG. 71 is a plan view of a still further embodiment of the present invention in which the gas sensitive layer is formed so as to be buried in the insulator layer.
Figure 72:
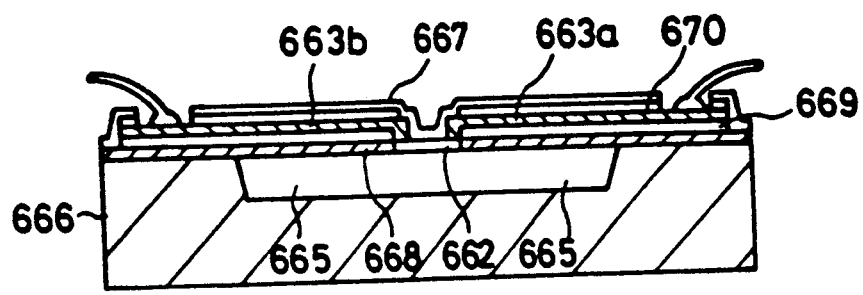
FIG. 72 is a cross sectional view taken along a line R—R' shown in FIG. 71.
Figure 73:
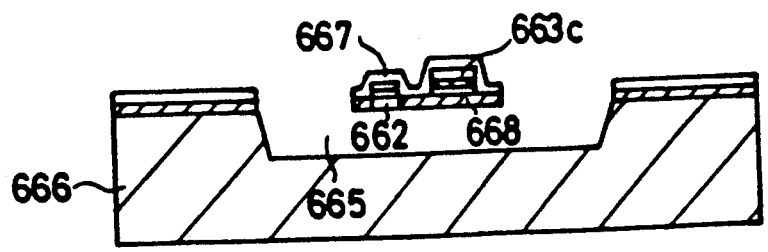
FIG. 73 is a cross sectional view taken along a line S—S' shown in FIG. 71.

In order to eliminate the above-mentioned problems, a structure shown in FIGS. 71 through 74 is now proposed. Referring to FIGS. 71 through 73, a silicon substrate 666 of a gas detector 661 has a cavity 665, above which an insulator layer 668 is formed. A gas sensitive layer 662 is formed so as to be buried in the insulator layer 668. On the insulator layer 668, there are formed detection leads 663a and 663b, and a heater lead 663c sandwiched by adhesion reinforcement layers 669 and 667 are formed. The detection leads 663a and 663b partially overlie the gas sensitive layer 662. The upper surface of the gas sensitive layer 662 is covered with an insulation coating layer 667. This is different from the above-mentioned embodiments. On the other hand, the bottom surface of the gas sensitive layer 662 is exposed to the cavity 665, or gas to be detected.

Figure 74:
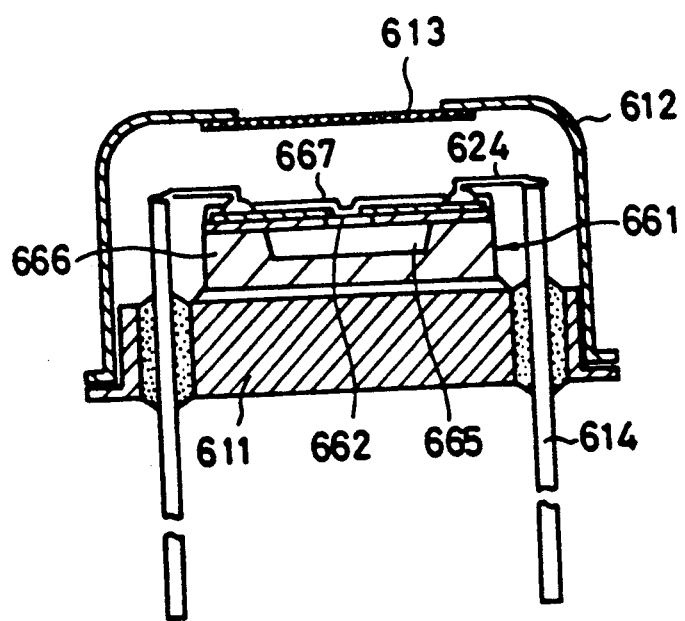
FIG. 74 is a view which illustrates hermetic seal of the present invention in which the gas detector shown in FIGS. 71 through 74 are used.
Figure 76E:
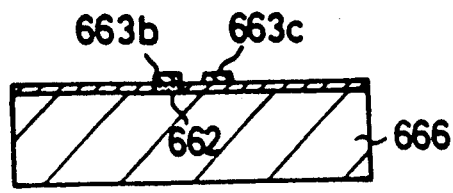

Referring to FIG. 74, the cap 612 having the stainless mesh 613 is mounted on the base 611. The bottom surface of the substrate 666 is fixed to the base 611 by an adhesive. The detection leads 663a and 663b are connected to wires 624 connected to the lead pin terminals 614. For the sake of simplicity, the adhesion reinforcement layers 669 and 670 shown in FIG. 72 are omitted. It is noted that there is no need for turning the gas detector 661 upside down. The upper surface of the gas sensitive layer 662 is totally covered with the insulation coating layer 667, whereby the influence of dust can be avoided. The gas sensitive surface of the gas sensitive layer 667 faces down, so that the gas sensitive layer 662 can be protected against dust.

A description is given of a method for producing the gas detector 661 with reference to FIGS. 75A through 75K and FIGS. 76A through 76J. In the gas detector described below, each of the detection leads and heater lead is constituted by a single layer without having adhesion reinforcement layers.

Figure 75E:
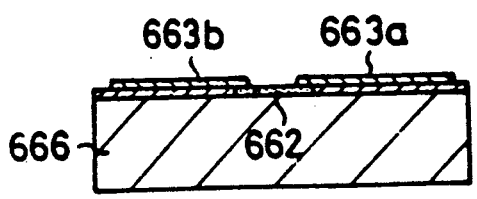
Figure 75F:
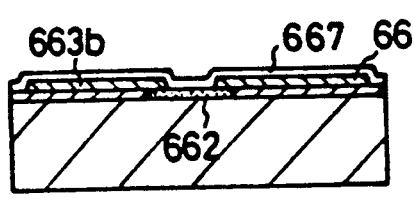
Figure 76F:
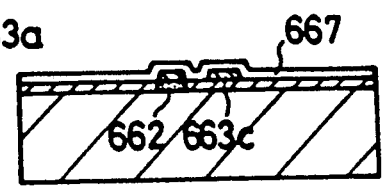
Figure 75G:
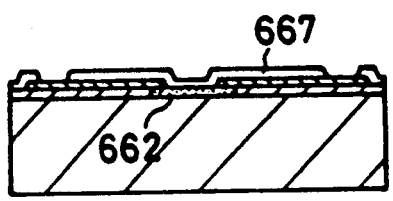
Figure 76G:
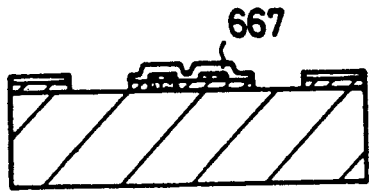
Figure 75H:
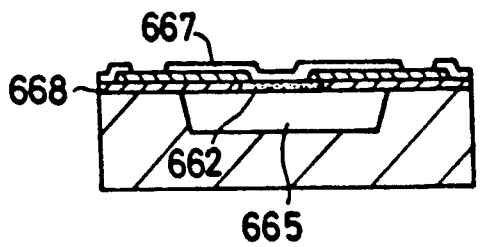
Figure 76H:
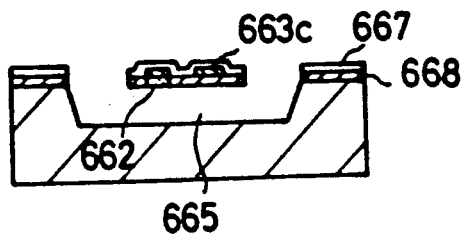

Referring to FIG. 75A and 76A, the gas sensitive layer is deposited on the silicon substrate 666 to a thickness of 0.05-2 μm, and is then patterned so as to obtain the gas sensitive layer 662. Next, as shown in FIGS. 75B and 76B, the insulator layer 668 is formed on the entire surface to a thickness of 0.1-2 μm. Then, as shown in FIGS. 75C and 76C, a portion of the insulator layer 668 on the gas sensitive layer 662 is removed by etching. Then, as shown in FIGS. 75D and 76D, detection leads 663a and 663b, and the heater lead 663c are formed on the insulator layer 668. End portions of the detection leads 663a and 663b overlie the gas sensitive layer 662. Subsequently, as shown in FIGS. 75F and 76F, the insulation coating layer 667 is formed on the entire surface of the silicon substrate 666 to a thickness of 0.1-2 μm. Then, the insulation coating layer 667 is partially etched so as to form openings for exposing bonding pad portions of the detection leads 663a and 663b, and forming the cavity 665 and so on. Finally, as shown in FIGS. 75H and 76H, the silicon substrate 666 is etched through the opening formed in the preceding step. In places of steps with respect to FIGS. 75A through 75C and FIGS. 76a through 76C, steps shown in FIGS. 75I through 75K and FIGS. 76I through 76J may be used.

Another gas detector and a method for producing the same are described with reference to FIGS. 77A through 77E and FIGS. 78A through 78E. Referring to FIGS. 77A and 78A, an insulator layer 678 of silicon dioxide and the conductive layer 673 are formed in this order on the silicon substrate 671. Next, as shown in FIGS. 77B and 78B, the conductive layer 673 and the insulator layer 678 are patterned by plasma etching. Then, as shown in FIG. 77C and 78C, the gas sensitive layer is formed on the entire surface of the silicon substrate 671, and is then patterned by photoetching. It is noted that in this etching, the gas sensitive layer 672 partially remains on the insulator layer 678. Subsequently, as shown in FIGS. 77D and 78D, the insulation coating layer 677 is formed on the entire surface, and is then partially etched so as to form openings. Finally, the silicon substrate 77E and 78E is etched so as to form the cavity 675 therein.

It is noted that other variations can be made by totally covering the aforementioned gas sensitive layers such as 452, 462, 472 and 482 with insulation coating layers.

A description is given of a process of depositing a gas sensitive layer on a substrate or an insulator layer.

As described previously, a gas sensitive layer can be formed by evaporation, chemical vapor deposition, sputtering or ion plating. For example, the following document discloses a process of heating a metal oxide material by a resistor heater and depositing them on a substrate or an insulator film: (i) T. Oyabu, J. Appl. Phys., 53, 2785, 1982. The U.S. Pat. No. 4,358,950 (ii) discloses the use of RF sputtering in which a metal oxide target is used. The following document discloses a process of generating a high-frequency electromagnetic field between an evaporation source and an object on which a gas sensitive layer is to be formed (iii) H. Ogawa, A. Abe, et al., The electrochemical Society Vol. 128, No. 9, 2020, 1981. The following paper discloses the formation of a metal oxide film by a spray method (iv) H. Pink, et al., J. Appl. Phys., 19, 513, 1980.

However, the above-mentioned method (i) has a disadvantage that it is difficult to obtain good step coverage in a case where tin dioxide is used as an evaporation source, because evaporation is performed in a highly-vacuumed gas. Additionally, tin dioxide does not have good sensitivity with respect to gas used in the evaporation process.

The method (ii) has a disadvantage of a low film growth rate and low mass productivity. The method (iii) has a disadvantage that a film formed by this method is soft, and adhesion thereof with respect to an underlying layer is not good. The method (iv) has a disadvantage a problem in which it is difficult to control the film component and film thickness.

The present inventors found that a thin-film evaporation apparatus disclosed in the Japanese Laid-Open Patent Application 59-89763 is suitable for forming gas sensitive layers with high mass productivity and good properties.

Figure 79A:
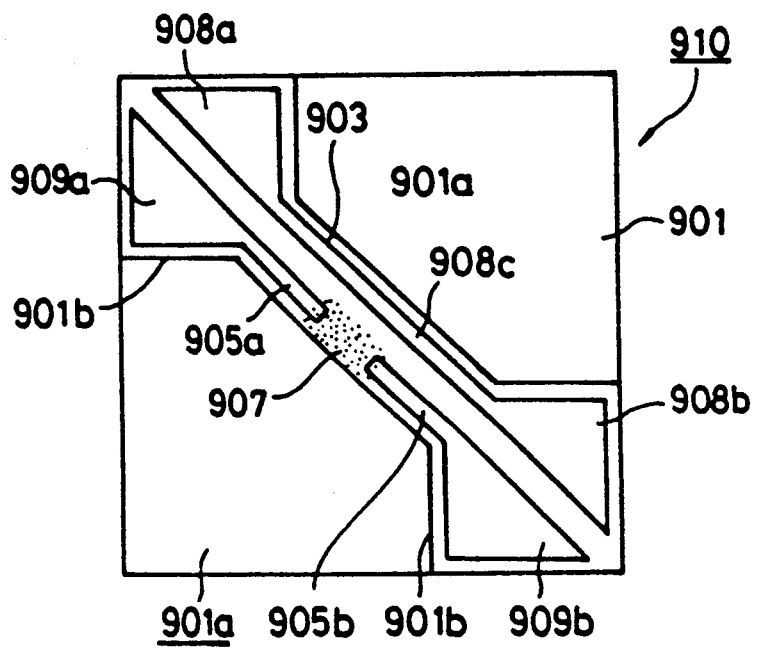
FIGS. 79A through 79C are views of a gas detector in which a gas sensitive layer is formed by using an apparatus illustrated in FIG. 83.
Figure 79B:
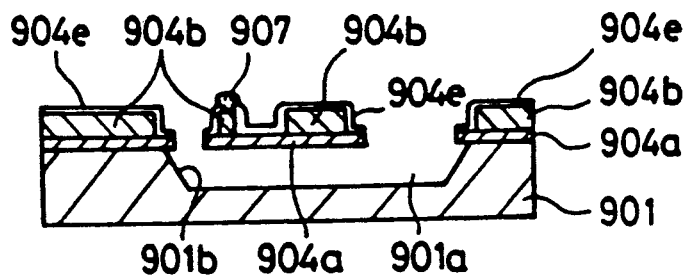
Figure 79C:
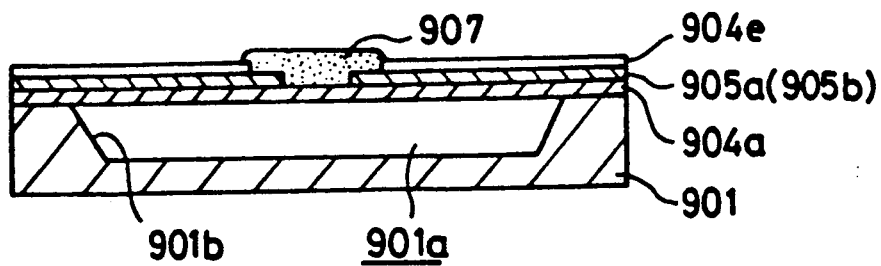

The present inventors fabricated a gas detector shown in FIGS. 79A, 79B and 79C by using the above-mentioned thin-film evaporation apparatus. The illustrated gas detector has the conventional structure as disclosed in the Japanese Laid-Open Patent Application No. 61-191953.

Referring to FIGS. 79A, 79B and 79C, a gas detector 910 comprises a silicon substrate 901 having projections or corner portions 901b. The substrate 901 has also a recess or a cavity 901a. An insulator layer 904a extends over the corner portions 901b. A gas sensitive layer 907 is formed on the insulator layer 907, to which a pair of detection leads 905a and 905b are connected. The gas detection leads 905a and 905b have bonding pad portions 909a and 909b, respectively. A heater lead 908c is formed on the insulator layer 904a so as to be arranged in parallel to the detection leads 905a and 905b. An insulator layer 904e is formed as shown in FIGS. 79A, 79B and 79C.

Figure 80A:
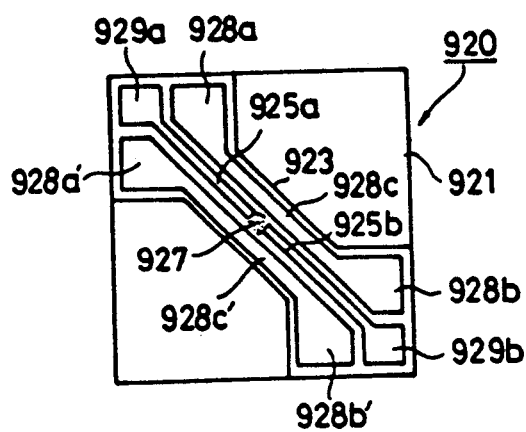
FIGS. 80A and 80B are views of a gas detector in which a gas sensitive layer is formed by using the apparatus illustrated in FIG. 83.
Figure 80B:
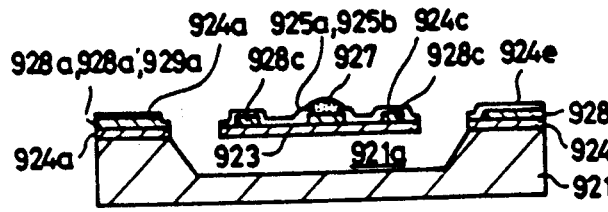

Referring to FIGS. 80A and 80B, a gas detector 920 comprises a silicon substrate 921 having a cavity 921a, and an insulator layer indicated by 923 and 924a. On the insulator layer 923, there are formed a gas sensitive layer 927, detection leads 925a and 925b, and heater leads 928c and 928c'. An insulator layer 924e is formed as shown. Reference numerals 928a, 928a', 928b, 928b', 929a and 929b indicate bonding pads.

Figure 81A:
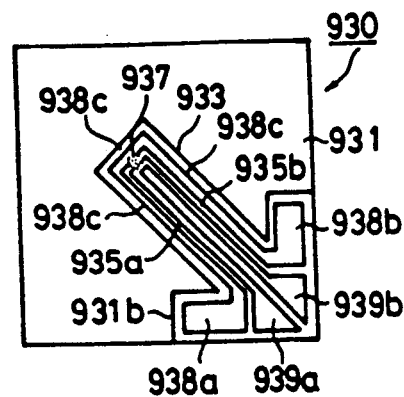
FIGS. 81A and 81B are views of a gas detector in which a gas sensitive layer is formed by using the apparatus illustrated in FIG. 83.
Figure 81B:
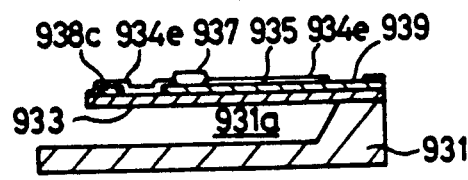

Referring to FIGS. 81A and 81B, a gas detector 930 comprises a silicon substrate 931 having a cavity 931a, and an insulator layer 933. On the insulator layer 933, there are formed a gas sensitive layer 937, detection leads 935a and 935b, and a heater lead 938c. An insulator layer 934e is formed as shown. Reference numerals 938a, 938b, 939a and 939b indicate bonding pads.

Figure 82:
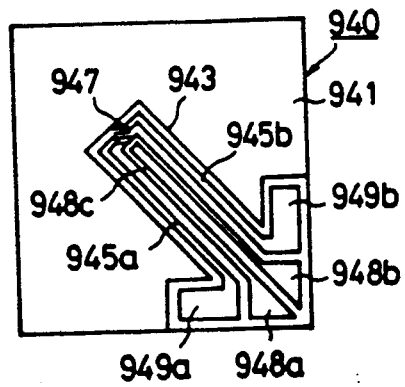
FIG. 82A is a view of a gas detector in which a gas sensitive layer is formed by using the apparatus illustrated in FIG. 83.

Referring to FIG. 82, a gas detector 940 comprises a silicon substrate 941, and an insulator layer 943. On the insulator layer 943, there are formed a gas sensitive layer 947, detection leads 945a and 945b, and a heater lead 948c. An insulator layer 944e is formed as shown. Reference numerals 948a, 948b, 949a and 949b indicate bonding pads.

Figure 83:
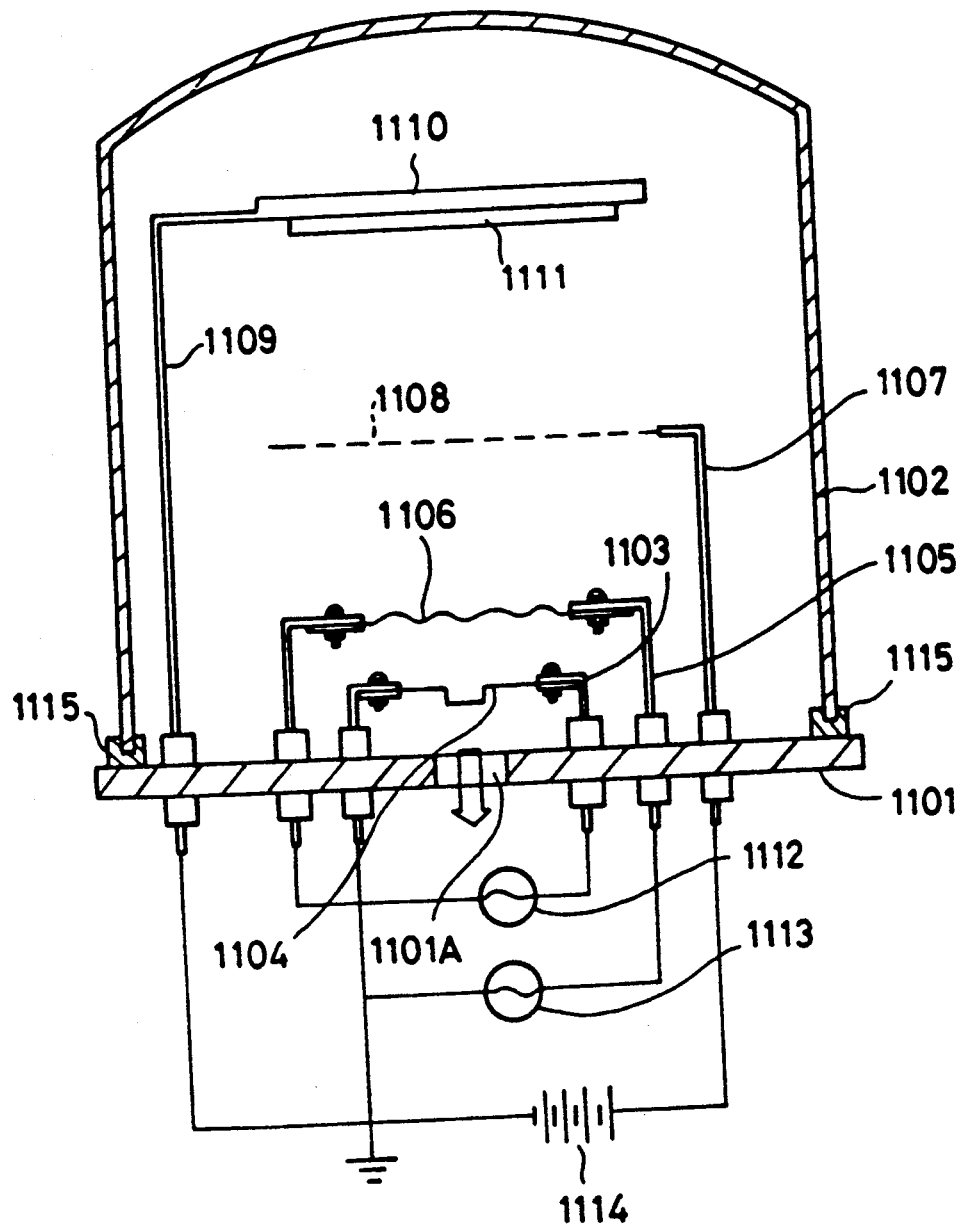
FIG. 83 is a view of the apparatus disclosed in the Japanese Laid-Open Patent Application No. 59-89763.

The gas sensitive layers 907, 927, 937 and 947 are formed by using the apparatus shown in FIG. 83. The apparatus includes an evaporation source 1104 for evaporating a material. An opposed electrode 1110 is provided so as to be opposite to the evaporation source 1104. A substrate 1111 is supported on the opposed electrode 1110. A grid 1108 is interposed between the opposed electrode 1110 and the evaporation source 1104. A filament 1106 is interposed between the grid 1108 and the evaporation source 1104, and is closed to the evaporation source 1104 than the grid 1108. The filament 1106 generates thermal electrons between the grid 1108 and the evaporation source 1104. The above-mentioned elements are installed in a vacuum chamber 1102. A power source 1114 is connected between the grid 1108 and the opposed electrode 1110. A positive voltage is supplied to the grid 1108. The vacuum chamber 1102 is supplied with an oxygen gas or a mixture gas of oxygen and an inactive gas such as argon. The evaporation source 1104 is constituted by a board or a coil which are made of tungsten or molybdenum. Alternatively, the evaporation source 1104 may be constituted on the basis of a beam evaporation method.

The grid 1108 is kept at a potential which is positive with respect to the opposed electrode 1110 and the filament 1106. Therefore, the electric field oriented toward the substrate 1110 is generated. Thermal electrons generated due to the function of the filament 1106 contributes to ionizing the gas in the vacuum chamber 1102 and some evaporated material.

A description is given of a method for growing a tin dioxide film on the substrate 1111. One of Sn, SnO and $SnO_2$ is supported to the evaporation source 1104. The degree of vacuum in the vacuum chamber 1102 is set on the order of $10^{-4}$Pa in advance. Oxygen gas is introduced in the chamber 1102, and is kept at a pressure of 0.1 Pa. In this state, the opposed electrode 1110 is set equal to zero volt, and a voltage of 100 volts is applied to the grid 1108. Further, the filament 1106 is supplied with a power of 400 watts. Some tin is ionized, and is then combined with oxygen, so that a tin dioxide film is formed on the substrate 1111.

The gas pressure in the vacuum chamber 1102 which enables the film growth is $1 \times 10^{-2}$ to 20 Pa. The voltage applied to the grid 1108 is in a range of 50 to 300 volts, preferably 70 to 150 volts. The power supplied to the filament 1106 is in a range of 50 to 500 watts, preferably 250 to 500 watts. The above-mentioned conditions may be used to form the other embodiments describe previously.

The present invention is not limited, and variations and modifications may be made without departing the scope of the present invention.

What is claimed is:

1. A gas detecting device comprising:
a substrate;
an insulator layer formed on said substrate;
a gas sensitive layer buried in said insulator layer;
a pair of detection leads formed on said insulator layer, said pair of detection leads partially overlying said gas sensitive layer, a signal derived from said gas sensitive layer being sent to an external circuit through said pair of detection leads;
a heater member arranged on said insulator layer in the vicinity of said gas sensitive layer; and
an insulation coating layer formed on said pair of detection leads and said heater member, a portion of an upper surface of said gas sensitive layer being exposed to gas through the pair of the detection leads.

2. A gas detecting device comprising:
a substrate having a cavity;
an insulator layer formed across said cavity formed in said substrate;
a gas sensitive layer buried in said insulator layer;
a pair of detection leads formed on said insulator layer, a signal derived from said gas sensitive layer being sent to an external circuit through said pair of detection leads, said pair of detection leads partially overlying said gas sensitive layer; and
an insulation coating layer formed on said pair of detection leads and the entire surface of said gas sensitive layer, a bottom surface of said gas sensitive layer facing said cavity, being served with a gas sensitive surface.

* * * * *